US012653764B2

(12) United States Patent
Gabbard et al.

(10) Patent No.: US 12,653,764 B2
(45) Date of Patent: Jun. 16, 2026

(54) BIODEGRADABLE MICROCAPSULES

(71) Applicants: INTERNATIONAL FLAVORS & FRAGRANCES INC., New York, NY (US); RENSSELAER POLYTECHNIC INSTITUTE, Troy, NY (US)

(72) Inventors: Ronald Gabbard, Holmdel, NJ (US); Julie Ann Wieland, Edison, NJ (US); Yabin Lei, Holmdel, NJ (US); Evan Beach, Fanwood, NJ (US); Crystal Kunzel, Barnegt, NJ (US); Richard Alan Gross, Troy, NY (US); Xue Wang, Troy, NY (US)

(73) Assignees: INTERNATIONAL FLAVORS & FRAGRANCES INC., New York, NY (US); RENSSELAER POLYTECHNIC INSTITUTE, Troy, NY (US)

( * ) Notice: Subject to any disclaimer, the term of this patent is extended or adjusted under 35 U.S.C. 154(b) by 275 days.

(21) Appl. No.: 18/694,024

(22) PCT Filed: Sep. 22, 2022

(86) PCT No.: PCT/US2022/044379

§ 371 (c)(1),
(2) Date: Mar. 21, 2024

(87) PCT Pub. No.: WO2023/049260

PCT Pub. Date: Mar. 30, 2023

(65) Prior Publication Data

US 2025/0000761 A1 Jan. 2, 2025

(30) Foreign Application Priority Data

Sep. 23, 2021 (EP) .................................... 21198609

(51) Int. Cl.
*C11D 3/37* (2006.01)
*A61K 8/11* (2006.01)
(Continued)

(52) U.S. Cl.
CPC .................. *A61K 8/11* (2013.01); *A61K 8/84* (2013.01); *A61Q 19/00* (2013.01); *B01J 13/16* (2013.01);
(Continued)

(58) Field of Classification Search
CPC ....... C11D 3/37; C11D 3/3723; C11D 3/3746; C11D 3/50; C11D 7/26; C11D 7/3209; C11D 17/0039
(Continued)

(56) References Cited

U.S. PATENT DOCUMENTS

| | | | | |
|---|---|---|---|---|
| 10,434,047 B2 * | 10/2019 | Latta | A61Q 19/00 | |
| 2014/0044761 A1 * | 2/2014 | Lei | C11D 3/505 424/70.13 | |

(Continued)

OTHER PUBLICATIONS

Anthony Maiorana et al, "Bio-Based Alternative to the Diglycidyl Ether of Bisphenol A with Controlled Materials Properties", Biomacromolecules, Feb. 12, 2015, vol. 16, No. 3, pp. 1021-1031.

*Primary Examiner* — Gregory R Delcotto

(57) ABSTRACT

This disclosure relates to biodegradable core-shell microcapsule compositions wherein the microcapsule shell contains a polymer formed with a biobased epoxide and a polyamine. This disclosure also relates to a method of preparing such biodegradable core-shell microcapsules. This disclosure also relates to consumer products containing such biodegradable core-shell microcapsules.

17 Claims, 1 Drawing Sheet

(51) Int. Cl.

| | |
|---|---|
| ***A61K 8/84*** | (2006.01) |
| ***A61Q 19/00*** | (2006.01) |
| ***B01J 13/16*** | (2006.01) |
| ***C11D 3/00*** | (2006.01) |
| ***C11D 3/50*** | (2006.01) |
| ***C11D 17/00*** | (2006.01) |

(52) U.S. Cl.
CPC ............ *C11D 3/001* (2013.01); *C11D 3/3707* (2013.01); *C11D 17/0039* (2013.01); *A61K 2800/10* (2013.01)

(58) Field of Classification Search
USPC ................................ 510/101, 296, 441, 475
See application file for complete search history.

(56) References Cited

U.S. PATENT DOCUMENTS

| | | | |
|---|---|---|---|
| 2020/0129947 | A1 | 4/2020 | Ouali et al. |
| 2021/0207317 | A1 | 7/2021 | Sasaki et al. |
| 2021/0237019 | A1 | 8/2021 | Bachawala et al. |

* cited by examiner

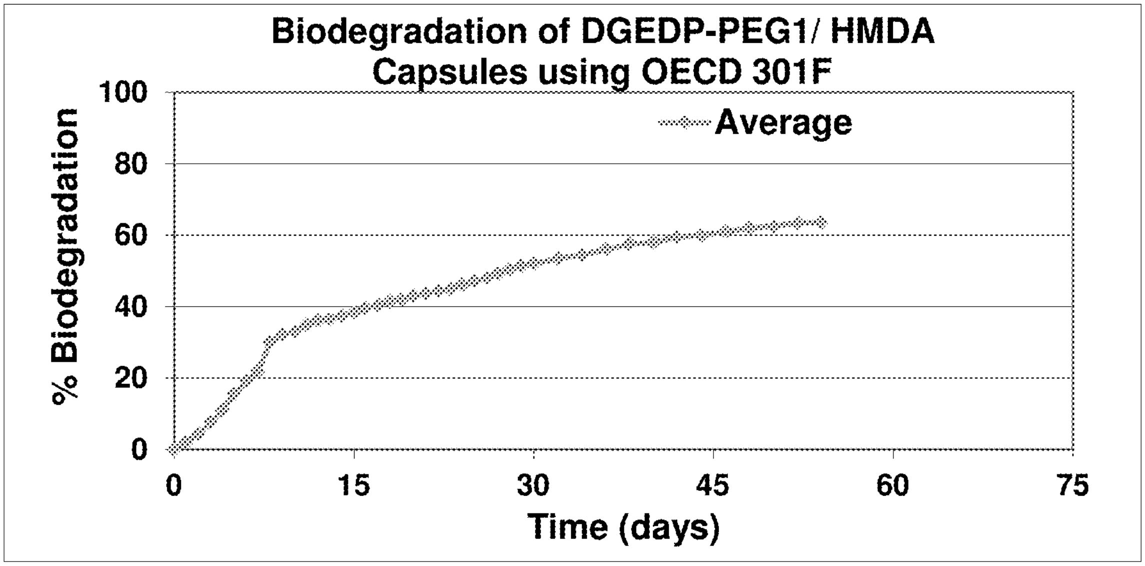
Biodegradation of DGEDP-PEG1/ HMDA
Capsules using OECD 301F
Average
% Biodegradation
0
20
40
60
80
100
0
15
30
45
60
75
Time (days)

BIODEGRADABLE MICROCAPSULES

FIELD OF THE INVENTION

The present disclosure relates to biodegradable core-shell microcapsule compositions wherein the microcapsule shell comprises a polymer formed with a biobased epoxide and a polyamine.

BACKGROUND OF THE INVENTION

Microencapsulation is a process of coating a core material with a continuous polymeric film, yielding small capsules ranging from one to several hundred microns in diameter (Ozkan, et al. (2019) *Food Chem.* 272:494-506; Bansode, et al. (2010) *Intl. J. Pharma. Sci. Rev. Res.* 1(2):38-43). Ideally, the core material is protected from the surrounding environment (e.g., heat, oxygen, moisture, UV radiation, interaction with other materials) and is released at desired conditions (Nikafshar, et al. (2017) *Materials* 10(2):180). Microencapsulated systems have attracted widespread interest in numerous fields such as foods, adhesives, pharmaceuticals, cosmetics, and textiles (Fadini, et al. (2018) *LWT* 91:345-352). Microencapsulated fragrances and essential oils are often incorporated in cosmetics and personal care products as odorants. Also, they are applied to textiles to prepare “functional textiles” with attributes such as self-cleaning, odor control and antimicrobials (Qiu, et al. (2020) *Chem. Eng. J.* 384:123241).

It has been reported that orange, lavender, rosemary, sage, and limonene oils containing volatile fragrance oils are retained in capsules for long time periods, thus prolonging the persistence of fragrances on textiles even after washing in a laundry detergent solution. Perfumes or fragrance oils are complex mixtures of various aroma compounds with different functional groups such as —OH, —NH, —C═O, —CHO or —COOH. Generally, fragrances and perfumes are composed of at least 50% top and middle notes. One of the problems encountered by fragrance industry lies in the relatively rapid evaporation and dissipation (e.g., within few hours) of olfactive benefit provided by fragrance compounds, particularly “top” and “heart” notes due to their higher volatility, if not encapsulated.

Consequently, a wealth of different microencapsulation methods has been used for the above-described applications. These techniques can be divided into three main categories: (1) physical-mechanical processes (e.g., spray drying and freeze drying); (2) physiochemical processes (e.g., simple and complex coacervation); and (3) chemical processes (e.g., interfacial and in situ polymerization). Among these microencapsulation techniques, spray drying is most frequently used for oil encapsulation since manufacturing processes are relatively simple and low cost. A limitation associated with spray drying is the low oxidative stability of products resulting from high temperatures used during atomization, especially for fragrance and essential oils that are known to be susceptible to oxidation. Freeze drying, is a low-temperature dehydration process that can increase materials oxidation stability; nevertheless, the high porosity of freeze-dried capsules exposes the core materials to the surrounding environment, limiting control of release properties.

Coacervation, another method for preparing oil microcapsules, entails a process in which a homogeneous solution of polymers undergoes liquid-liquid phase separation, leading to the formation of a polymer-rich phase covering the core droplets. Although coacervation techniques give high encapsulation efficiency, polymer films, formed exclusively by non-covalent ionic interactions and phase separation, result in low strength of microcapsule walls.

The formation of microcapsule walls through chemical processes such as interfacial and in situ polymerization can provide both high encapsulation efficiency and strong wall mechanical strength. Interfacial polymerization typically involves reactions between oil-soluble and water-soluble components to form polymeric microcapsules, whose dimensions are determined by the emulsion droplet size. For microencapsulation by in situ polymerization, no reactants are included in the core material, and the polymerization site resides on capsule walls in contact with the continuous phase rather than at the interface between two immiscible phases. Microencapsulation by in situ polymerization has been used for capsule payloads including peppermint, thyme, tea tree oils, fragrances, insect repellent and footwear applications. Furthermore, interfacial polymerization has been used to microencapsulate a wide range of fragrance oils within various polymeric shells, mostly polyureas, since the isocyanate groups readily react with nucleophilic functionalities.

Although interfacial and in situ polymerizations have been used extensively for microcapsule preparation, current limitations include: (1) large quantities of residual solvent; (2) capsule building blocks are often not biodegradable or biocompatible, and some (e.g., formaldehyde and isocyanate) are toxic in their unreacted form, endangering workers who can suffer severe health issues such as skin burns, suffocation, and cancer. There is increased pressure on microcapsule manufacturers and users to develop microcapsules following green chemistry principles, using biodegradable materials to build capsule walls, and move toward capsules that are derived from biomass-based carbon sources.

Epoxy resins are typically used to prepare coatings, adhesives, composite manufacturing, aerospace industry, electronic materials, and biomedical systems. The most ubiquitous component of epoxy resins is the diglycidyl ether of bisphenol A (DGEBA) that forms high-performance thermoset resins when cured (Maiorana, et al. (2015) *Biomacromolecules* 16 (3):1021-1031). DGEBA is synthesized industrially through the reaction of bisphenol A (BPA) with a large excess of epichlorohydrin under alkaline conditions; however, BPA, which has structural similarities to estrogens, is considered an endocrine disruptor that's been linked to reduced fertility, cancer, diabetes, obesity, cardiovascular events, reproductive disorders and more.

Since 2013, the U.S. Federal Drug Administration (FDA) imposed a ban on the use of BPA in baby bottles and infant formula packaging. The perceived risks have sparked research to identify biobased safe epoxy resins to replace DGEBA in formulations. A series of diphenolic acid (DPA) esters have been developed via the condensation reaction of phenol with levulinic acid. Levulinic acid is produced by cellulose hydrolysis under acidic conditions and phenol is expected to be available as a lignin by-product. While DPA is similar to BPA in structure, its relative binding affinity to estrogen receptors is an order of magnitude lower than BPA, leading to a lower risk of endocrine disrupting effects. It has been demonstrated that diglycidyl ether modified DPA-esters (DGEDP-esters), when cured with a diamine hardener, demonstrate mechanical and thermal properties that are comparable to that of DGEBA resins crosslinked under identical conditions (Maiorana, et al. (2015) *Biomacromolecules* 16 (3):1021-1031).

To date, epoxy resins are not commonly used as components in microcapsules. For example, EP 1871948 B1 describes a microcapsule with a shell based on urea-formaldehyde, melamine-formaldehyde, polyamide, or chitosan, wherein the shell includes reactive functional groups for chemical binding to a textile fiber, said reactive functional groups being introduced by reacting an amino or hydroxyl group of the shell with a bifunctional epoxy group, halogen-substituted alkyl group, vinyl group or heterocyclic group. However, EP '948 B1 does not describe the biobased epoxy according to the present disclosure nor how to formulate it into the microcapsules.

Therefore, there is a need in the fragrance industry for delivery systems which have improved biodegradability, preferably the reactant structures give a biodegradable shell, to provide ecological and/or sustainable fragrance compositions and consumer products comprising said fragrance compositions. In addition to biodegradability, it is desirable that the delivery system also provide a certain degree of stability to minimize fragrance leakage from the delivery system and/or preferably also provide a desirable fragrance impression upon release to the consumer at various tailored release touch points.

SUMMARY OF THE INVENTION

This invention is based, inter alia, on the discovery that the shell of a core-shell microcapsule composition comprising a polymer formed with a biobased epoxide and a polyamine is essentially biodegradable, particularly as measured by the OECD301F test. Furthermore, the core-shell microcapsule compositions of the present disclosure have sufficient stability in challenging bases (e.g., aggressive surfactant systems) without physically dissociating or degrading and/or suitable performance to enable their formulation into various consumer products, particularly, high-demand fields such as fabric detergents/conditioners and personal/household cleaners.

Thus, according to a first aspect, the present disclosure provides a core-shell microcapsule composition comprising: (i) a microcapsule core comprising an active material; and (ii) a microcapsule shell encapsulating the microcapsule core; wherein the microcapsule shell comprises a polymer formed with a biobased epoxide and a polyamine, and wherein the biobased epoxide is a diglycidyl ether diphenolic ester, preferably the biobased epoxide is selected from the group consisting of diglycidyl ether diphenolic methyl ester, diglycidyl ether diphenolic ethyl ester, diglycidyl ether diphenolic propyl ester, diglycidyl ether diphenolic butyl ester, diglycidyl ether diphenolic pentyl ester, diglycidyl ether diphenolic methoxy PEG, and combinations thereof, wherein the PEG is a PEG having 1 to 10 ethylene oxide units, preferably the PEG has 1 ethylene oxide unit. In some embodiments, the microcapsule shell does not comprise or is substantially free of an isocyanate. In some embodiments, the microcapsule shell does not comprise or is substantially free of a self-condensing polyisocyanate. In some embodiments, the microcapsule shell does not comprise or is substantially free of a polyisocyanate. In some embodiments, the microcapsule shell does not comprise or is substantially free of urea functional group or polyurea. In some embodiments, the microcapsule shell does not comprise or is substantially free of urethane functional group or polyurethane. In some embodiments, the microcapsule shell does not comprise or is substantially free of silane (e.g., organofunctional silane) and/or self-condensed silane. In some embodiments, the microcapsule shell does not comprise or is substantially free of Si—O—Si functional group. As used herein, the term "substantially free" means comprising no more than 2%, 1%, 0.5%, 0.2%, 0.1%, 0.05%, 0.02% or 0.01% by weight. In some embodiments, the polymer formed with the biobased epoxide and the polyamine is the only or single kind of polymer present in the microcapsule shell. A person having ordinary skill in the art appreciates that residual unreacted polyamine may also be present in the microcapsule shell.

In some aspects, the polymer is formed by an interfacial polymerization of the biobased epoxide and the polyamine. In some aspects, the polyamine is selected from the group consisting of hexamethylene diamine (HMDA), ethylene diamine (EDA), diethylene triamine (DETA), dihydrazide, dipropylenetriamine (norspermidine), triethylene tetramine (TETA), tetraethylene pentamine (TEPA), chitosan oligosaccharide (COS), guanidine carbonate, ε-poly(L-lysine), α-poly(L-lysine), L-lysine containing peptides, L-lysine containing proteins, gelatin, and combinations thereof. In some embodiments, the dihydrazide is selected from the group consisting of adipic acid dihydrazide, isophthalic dihydrazide, terephthalic dihydrazide, suberic acid dihydrazide, sebacic dihydrazide, malonic acid dihydrazide, 2-hydroxypropane-1,2,3-tricarbohydrazide, and combinations thereof. In some embodiments, the dihydrazide is adipic acid dihydrazide and/or suberic acid dihydrazide.

In further aspects, the polyamine is selected from the group consisting of hexamethylene diamine (HMDA), chitosan oligosaccharide (COS), guanidine carbonate, and combinations thereof, preferably the COS has an average molecular weight of less than or equal to 20,000 Da. Preferably, the polyamine is a combination of HMDA and COS or a combination of HMDA and guanidine carbonate, wherein the weight ratio of HMDA to COS is from 10:1 to 1.5:1 and preferably from 2:1 to 1.5:1 or from 10:1 to 2:1, and the weight ratio of HMDA to guanidine carbonate is from 10:1 to 1.5:1 and preferably from 2:1 to 1.5:1 or from 10:1 to 2:1.

In certain aspects, the microcapsule has a mean diameter particle size of from 5 μm to 100 μm, preferably from 10 μm to 75 μm, or more preferably from 10 μm to 50 μm, as determined by dynamic light scattering. In other aspects, the total amount of the active material ranges from 5% to 50%, preferably from 10% to 50% or more preferably from 15% to 30% by weight of the core-shell microcapsule composition.

In still other aspects, the weight ratio of the active material to the biobased epoxide is from 50:1 to 1:1, preferably from 30:1 to 4:1. Preferably, the active material is selected from the group consisting of fragrance, flavor, cosmetic active, malodor counteractant, and combinations thereof, preferably the active material is a fragrance oil. Desirably, the microcapsule shell is biodegradable, preferably biodegradable according to OECD301F test, OECD310 test, OECD302 test, OECD307 test, OECD308 test, OECD309 test, ISO 17556 test, ISO 14851 test, or ISO 18830 test, more preferably the microcapsule shell has a degree of biodegradability of at least 20%, 30%, 40%, 50%, 60%, 65%, 70%, 75%, 80%, 85%, 90%, 95% or 98%, within 60 days according to OECD301F test. Preferably the microcapsule shell is inherently primary biodegradable as evidenced by a degree of biodegradability of at least 20% according to OECD 301F test, or ultimately biodegradable as evidenced by a degree of biodegradability of at least 60% according to OECD 301F test. Because of the biodegradability and stability and/or performance of this microcapsule, it can be used in many consumer products.

Consequently, according to another aspect the present disclosure relates to a consumer product comprising the biodegradable core-shell microcapsule according to any one of the foregoing aspects, wherein the consumer product is a laundry detergent, a liquid laundry detergent, a powder laundry detergent, a tablet laundry detergent, a mono-chamber or multi-chamber unidose detergent, a laundry detergent bar, a laundry detergent cream, a hand wash laundry detergent, a fabric conditioner or softener, a dryer sheet, a fabric refresher, a liquid or solid scent booster, a shampoo, a hair conditioner, a bar soap, a shower gel, a body wash, an antiperspirant, a deodorant, a body spray, a body mist, a lotion, a candle or a textile, preferably a fabric conditioner or softener having a pH of from 2 to 4, preferably a pH of from 2.5 to 3.5.

In yet another aspect, the present disclosure further provides a method of preparing a core-shell microcapsule composition according to any one of the foregoing aspects. The method comprises: (a) emulsifying an active material with a biobased epoxide to form an emulsion, wherein the biobased epoxide is a diglycidyl ether diphenolic ester, preferably the biobased epoxide is selected from the group consisting of diglycidyl ether diphenolic methyl ester, diglycidyl ether diphenolic ethyl ester, diglycidyl ether diphenolic propyl ester, diglycidyl ether diphenolic butyl ester, diglycidyl ether diphenolic pentyl ester, diglycidyl ether diphenolic methoxy PEG, and combinations thereof, wherein the PEG is a PEG having 1 to 10 ethylene oxide units, preferably the PEG has 1 ethylene oxide unit; (b) adding a polyamine to the emulsion, preferably the polyamine is selected from the group consisting of hexamethylene diamine (HMDA), ethylene diamine (EDA), diethylene triamine (DETA), dihydrazide, dipropylenetriamine (norspermidine), triethylene tetramine (TETA), tetraethylene pentamine (TEPA), chitosan oligosaccharide (COS), guanidine carbonate, ε-poly(L-lysine), α-poly(L-lysine), L-lysine containing peptides, L-lysine containing proteins, gelatin, and combinations thereof, preferably the COS has an average molecular weight of less than or equal to 20,000 Da; and (c) providing a condition sufficient to induce interfacial polymerization in the emulsion to form a slurry that comprises core-shell microcapsules each having a microcapsule shell encapsulating a microcapsule core, thereby obtaining the core-shell microcapsule composition according to any of the foregoing aspects. In some aspects, the dihydrazide is selected from the group consisting of adipic acid dihydrazide, isophthalic dihydrazide, terephthalic dihydrazide, suberic acid dihydrazide, sebacic dihydrazide, malonic acid dihydrazide, 2-hydroxypropane-1,2,3-tricarbohydrazide, and combinations thereof. In some aspects, the dihydrazide is adipic acid dihydrazide and/or suberic acid dihydrazide. In some aspects, the slurry comprising core-shell microcapsules is cured for up to 24 hours. In other aspects, the emulsion further comprises an emulsifier, preferably the emulsifier is selected from the group consisting of gum Arabic, polyvinyl alcohol, sophorolipid butyl ester, polyvinyl pyrrolidone, polyquaternium-11, and combinations thereof. In other aspects, the microcapsule shell is biodegradable, preferably biodegradable according to OECD301F test, OECD310 test, OECD302 test, OECD307 test, OECD308 test, OECD309 test, ISO 17556 test, ISO 14851 test, or ISO 18830 test, more preferably the microcapsule shell has a degree of biodegradability of at least 20%, 30%, 40%, 50%, 60%, 65%, 70%, 75%, 80%, 85%, 90%, 95% or 98%, within 60 days according to OECD301F test.

In yet another aspect, the present disclosure further provides a method for increasing the degree of biodegradability of a core-shell microcapsule. The method comprises incorporating a polymer into the shell of the core-shell microcapsule to increase the degree of biodegradability of the core-shell microcapsule, wherein the polymer is formed with a biobased epoxide and a polyamine, wherein the biobased epoxide is a diglycidyl ether diphenolic ester, preferably the biobased epoxide is selected from the group consisting of diglycidyl ether diphenolic methyl ester, diglycidyl ether diphenolic ethyl ester, diglycidyl ether diphenolic propyl ester, diglycidyl ether diphenolic butyl ester, diglycidyl ether diphenolic pentyl ester, diglycidyl ether diphenolic methoxy PEG, and combinations thereof, wherein the PEG is a PEG having 1 to 10 ethylene oxide units, preferably the PEG has 1 ethylene oxide unit, wherein preferably the polyamine is selected from the group consisting of hexamethylene diamine (HMDA), ethylene diamine (EDA), diethylene triamine (DETA), dihydrazide, dipropylenetriamine (norspermidine), triethylene tetramine (TETA), tetraethylene pentamine (TEPA), chitosan oligosaccharide (COS), guanidine carbonate, ε-poly(L-lysine), α-poly(L-lysine), L-lysine containing peptides, L-lysine containing proteins, gelatin, and combinations thereof, preferably the COS has an average molecular weight of less than or equal to 20,000 Da, wherein the polymer is formed by interfacial polymerization in an emulsion, preferably the emulsion comprises an emulsifier, preferably the emulsifier is selected from the group consisting of gum Arabic, polyvinyl alcohol, sophorolipid butyl ester, polyvinyl pyrrolidone, polyquaternium-11, and combinations thereof.

In yet another aspect, the present disclosure provides for the use of biobased epoxide for increasing the degree of biodegradability of a microcapsule shell in a core-shell microcapsule composition, wherein a polymer formed with a biobased epoxide and a polyamine is incorporated into the microcapsule shell, preferably by interfacial polymerization of the biobased epoxide with the polyamine, to increase the degree of biodegradability of the microcapsule shell as compared to a microcapsule shell without said polymer, wherein the biobased epoxide is a diglycidyl ether diphenolic ester, preferably the biobased epoxide is selected from the group consisting of diglycidyl ether diphenolic methyl ester, diglycidyl ether diphenolic ethyl ester, diglycidyl ether diphenolic propyl ester, diglycidyl ether diphenolic butyl ester, diglycidyl ether diphenolic pentyl ester, diglycidyl ether diphenolic methoxy PEG, and combinations thereof, wherein the PEG is a PEG having 1 to 10 ethylene oxide units, preferably the PEG has 1 ethylene oxide unit, wherein preferably the polyamine is selected from the group consisting of hexamethylene diamine (HMDA), ethylene diamine (EDA), diethylene triamine (DETA), dihydrazide, dipropylenetriamine (norspermidine), triethylene tetramine (TETA), tetraethylene pentamine (TEPA), chitosan oligosaccharide (COS), guanidine carbonate, ε-poly(L-lysine), α-poly(L-lysine), L-lysine containing peptides, L-lysine containing proteins, gelatin, and combinations thereof, preferably the COS has an average molecular weight of less than or equal to 20,000 Da.

In a further aspect, the present disclosure provides for the use of a core-shell microcapsule composition for improving a freshness impression to a fabric by contacting the fabric with said core-shell microcapsule composition.

All parts, percentages and proportions referred to herein and in the claims are by weight unless otherwise indicated.

The values and dimensions disclosed herein are not to be understood as being strictly limited to the exact numerical values recited. Instead, unless otherwise specified, each such value is intended to mean both the recited value and a functionally equivalent range surrounding that value. For example, a value disclosed as "50%" is intended to mean "about 50%" or alternatively, for example, about ±2%, ±5%, ±10% or ±15% of that value.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. For example, when a range of "1 to 10" is recited, the recited range should be construed as including ranges "1 to 8", "3 to 10", "2 to 7", "1.5 to 6", "3.4 to 7.8", "1 to 2 and 7-10", "2 to 4 and 6 to 9", "1 to 3.6 and 7.2 to 8.9", "1-5 and 10", "2 and 8 to 10", "1.5-4 and 8", and the like.

While compositions and methods are described herein in terms of "comprising" various components or steps, the compositions and methods also can "consist essentially of" or "consist of" the various components or steps, unless stated otherwise.

The details of one or more aspects of the disclosure are set forth in the description below. Each of the aspects and embodiments described herein are capable of being used together, unless excluded either explicitly or clearly from the context of the embodiment or aspect. These and other features, objects, and advantages of the disclosure will be apparent to those skilled in the art from the detailed description and the drawing in conjunction with the appended claims.

BRIEF DESCRIPTION OF THE DRAWING

While the specification concludes with claims particularly pointing out and distinctly claiming the invention, it is believed that the invention will be better understood from the following description of the accompanying FIGURE wherein:

FIG. 1 shows biodegradation properties of capsules of an embodiment of the present disclosure prepared with DGEDP-PEG1 (diglycidyl ether diphenolic methoxy PEG1) and HMDA through OECD301F evaluation (Biodegradation Test that measures $O_2$ consumption) after up to 54 days, with samples of the capsules prepared according to the method described in this disclosure.

DETAILED DESCRIPTION OF THE INVENTION

Definitions

As used herein, articles such as "a" and "an" when used in a claim or disclosure, are understood to mean one or more of what is claimed or described.

As used herein, the term "biobased" refers to atoms or molecules obtained from biomass, e.g., obtained from materials containing organic carbon from a readily renewable source. Such carbon can be derived from agricultural products, plants, animals, fungi, microorganisms, marine, or forestry materials. The term "biodegradable" as used herein with respect to a material, such as a microcapsule shell and/or a polymer (e.g., biopolymer), means the material has no real or perceived health and/or environmental concerns, and can undergo microbial and/or biological degradation. Biodegradability means a materials capacity to undergo biological degradation by living organisms forming substances such as water, carbon dioxide, methane, basic elements and biomass.

Ideally, a microcapsule shell and/or polymer is deemed "biodegradable" when the microcapsule shell and/or polymer has a biodegradability measured according to Organization for Economic Cooperation and Development (OECD) tests, including OECD301F test ($O_2$ consumption), OECD310 test (Ready biodegradation), OECD302 test (inherent biodegradation), OECD307 test (soil stimulation studies), OECD308 test (sediment stimulation studies), or OECD309 test (water stimulation studies), or the International Organization for Standardization (ISO) tests including, ISO 17556 test (solid stimulation studies), ISO 14851 test (fresh water stimulation studies), or ISO 18830 test (marine sediment stimulation studies). Preferably, the biodegradability is measured using the OECD test methods whereby the test samples have undergone an additional washing protocol as described in the Examples section herein. As a result, the microcapsules are freed from dissolved residues (which may artificially enhance the biodegradability measure) by washing before the biodegradability is determined, and which allows for a more accurate measure of biodegradability versus current protocols (e.g., "Quantification of Residual Perfume by Py-GC-MS in Fragrance Encapsulate Polymeric Materials Intended for Biodegradation Tests," February 2020 *Molecules* 25(3):718.).

In some aspects, microcapsule shell or polymer contained therein having biodegradability of at least 20% or 40%, as measured according to OECD 301F test, is considered to be "inherently biodegradable", "inherently primary biodegradable" or "biodegradable". "Inherently biodegradable" refers to a classification of chemicals for which there is unequivocal evidence of biodegradation in any tests of biodegradability. "Primary biodegradation" refers to the alteration in the chemical structure of a substance, brought about by biological action, resulting in the loss of a specific property of that substance. In other aspects, microcapsule shell or polymer contained therein having biodegradability of at least 60%, as measured according to OECD 301F test, is considered to have "ultimate biodegradability". "Ultimate biodegradation" refers to the level of degradation achieved when the test compound is totally utilized by microorganisms resulting in the production of carbon dioxide, water, mineral salts and new micro cellular constituents (biomass). These characterizations of biodegradability correspond to the limit values set out in the "*Revised Introduction to the OECD Guidelines for Testing of Chemicals*, Section 3, Part 1, dated 23 Mar. 2006".

As used herein, the terms "capsule", "microcapsule" and "core-shell microcapsule" are used interchangeably and refer to substantially spherical structures with smooth surfaces having a well-defined core and a well-defined envelope or wall.

As used herein, the term "epoxide" refers to a substituted or unsubstituted oxirane.

As used herein, the terms "g," "mg," and "μg" refer to "gram," "milligram," and "microgram," respectively. The terms "L" and "mL" refer to "liter" and "milliliter," respectively.

As used herein, the terms "include", "includes" and "including" are meant to be non-limiting.

As used herein, the terms "shell" and "wall" are used interchangeably and refer to the shell enveloping the core material of the microcapsule.

The term "diglycidyl ether diphenolic ester", as used herein, is a chemical compound represented by the following structural formula (I):

(I)

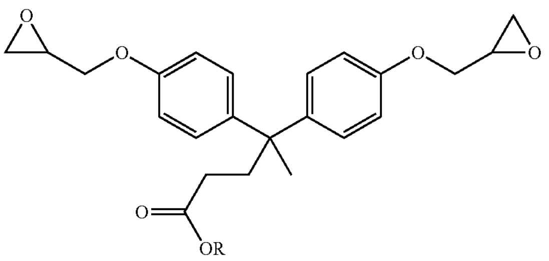

diglycidyl ether diphenolic ester wherein R is an alkyl group or an ethylene oxide unit(s) end capped with a methyl group as represented by the following structural formula (II):

(II)

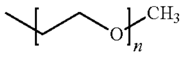

wherein n is an integer of from 1 to 10.

When R is methyl group, the structural formula (I) is diglycidyl ether diphenolic methyl ester; when R is ethyl group, the structural formula (I) is diglycidyl ether diphenolic ethyl ester; when R is n-propyl group, the structural formula (I) is diglycidyl ether diphenolic propyl ester; when R is n-butyl group, the structural formula (I) is diglycidyl ether diphenolic butyl ester; when R is n-pentyl group, the structural formula (I) is diglycidyl ether diphenolic pentyl ester; when R is structural formula (II), the structural formula (I) is diglycidyl ether diphenolic methoxy PEG.

Biodegradable Core-Shell Microcapsules

The inventors have surprisingly discovered that stable biodegradable core-shell microcapsules can be prepared from primarily biobased, safe, and biodegradable building blocks by interfacial polymerizations where the capsule walls stabilize the core oil phase. Specifically, at least one biobased epoxide was incorporated in the core material (fragrance oil), while a polyamine was added to the aqueous phase to trigger interfacial polymerization of the microcapsule walls. To stabilize oil-in-water emulsions during the microencapsulation process, while supporting interfacial polymerization, an emulsifier selected from the group consisting of gum Arabic (GA), polyvinyl alcohol (PVA), sophorolipid butyl ester (SLBE), polyvinyl pyrrolidone (PVP), polyquaternium-11 (PQ-11), and combinations thereof can be used in the emulsions.

The inventors also discovered that the capsules were stable under harsh conditions and demonstrated sufficient fragrance oil release properties required for consumer acceptance of the composition. Advantageously, the instant microcapsules provide an alternative to isocyanate or melamine-formaldehyde systems thus contributing to human health and the environment. In addition, the microcapsule composition delivery system of the present disclosure is suitable for utility in a wide range of consumer applications, in particular in fabric care applications such as fabric conditioners and laundry detergents.

Desirably, the microcapsules of the present disclosure are biodegradable. In certain aspects, the microcapsule shell has a degree of biodegradability of at least 20%, 30%, 40%, 50%, 60%, 65%, 70%, 75%, 80%, 85%, 90%, 95% or 98%, within 60 days according to OECD301F test or optionally OECD310 test. In other aspects, the microcapsule shell has a degree of biodegradability of at least 20%, 30% or 40% measured according to OECD301F test over a period of 28 days and is "inherently biodegradable", "inherently primary biodegradable" or "biodegradable". In further aspects, the microcapsule shell has a degree of biodegradability of at least 60% measured according to OECD301F test over a period of 60 days and is considered to have "ultimate biodegradability". The inventors submit that the biodegradability of the microcapsule shells is achieved, in part, due to the use of natural components in the wall. However, the incorporation of certain percentage of natural potentially biodegradable components does not automatically lead to a corresponding high value of biodegradability. Without wishing to be bound by theory, inventors submit that the biodegradability depends on the careful selection of the biobased epoxide and its specific reaction with components used for encapsulation present in the shell.

Conventional synthetic microcapsules are non-biodegradable. For example, polyurea-based microcapsules are prepared by first dissolving a polyisocyanate in an oil phase and then emulsifying the oil phase with an aqueous phase containing polyamines, polyelectrolytes or biopolymers thereby promoting the reaction of the polymers at the oil-water interface. While the intended reaction is an interfacial polymerization, controlling the kinetics to yield a copolymer/composite is difficult. It has been observed that capsules prepared via this traditional method yield a blend of polyurea formed from the self-condensation of polyisocyanate coated with a layer of unreacted material originally intended for the interfacial polymerization. The issue with such capsules is that the shell, even though they may pass the OECD301F or OECD310 tests, may still not be 'truly' biodegradable, for example under proposed ECHA legislation, because it is considered a blend of biodegradable (i.e., biobased epoxide) and non-biodegradable materials (i.e., self-condensing polyisocyanate). In some embodiments, the microcapsule composition of the present disclosure does not comprise a blend of biodegradable and non-biodegradable materials. As used herein, the term "blend" means mixtures of the biodegradable and non-biodegradable materials present in a weight ratio of from 100:1 to 1:100. In some embodiments, the microcapsule composition of the present disclosure comprises no more than 2%, 1%, 0.5%, 0.2%, 0.1%, 0.05%, 0.02% or 0.01% self-condensing polyisocyanate, based on the weight of the microcapsule composition. In some embodiments, the microcapsule composition of the present disclosure comprises no more than 7%, 6%, 5%, 4%, 3%, 2%, 1%, 0.5%, 0.2%, 0.1%, 0.05%, 0.02% or 0.01% non-biodegradable material, based on the weight of the microcapsule composition. In some embodiments, the microcapsule composition of the present disclosure does not comprise a non-biodegradable materials.

In accordance with the present disclosure, the core of the microcapsule comprises at least one active material. In other aspects, the core of the microcapsule comprises more than one active material. An active material for inclusion in the core of the microcapsule is preferably a fragrance, a flavor, a cosmetic active, a malodor counteractant, or a combination thereof. In certain aspects, the active material is a fragrance oil. Suitable active materials are further described, e.g., in WO 2016/049456, pages 38-50. In some aspects, the active material may be combined with a core modifier which is a hydrophobic substance, for example caprylic/capric triglyceride oil (NEOBEE® oil) or white mineral oil.

In some aspects, the total amount of the active material ranges from 5% to 50% by weight of the core-shell microcapsule composition. Preferably, the total amount of the active material ranges from 10% to 50%, preferably from 15% to 30% by weight of the core-shell microcapsule composition.

In other aspects, the weight ratio of the active material to the biobased epoxide is from 50:1 to 1:1, preferably from 30:1 to 4:1. A higher ratio will allow for higher fragrance load mitigating capsule cost while lower ratio will create a more robust capsule wall. The ratio can be determined by the harshness of the application and cost needed to meet consumer appeal and performance needs.

The wall of the microcapsule of the present disclosure comprises a polymer formed with a biobased epoxide and a polyamine. In certain aspects, the biobased epoxide is a diglycidyl ether diphenolic ester. In particular aspects, the biobased epoxide is a diglycidyl ether diphenolic ester selected from the group consisting of diglycidyl ether diphenolic methyl ester, diglycidyl ether diphenolic ethyl ester, diglycidyl ether diphenolic propyl ester, diglycidyl ether diphenolic butyl ester, diglycidyl ether diphenolic pentyl ester, diglycidyl ether diphenolic methoxy PEG, and combinations thereof.

For the purposes of the present disclosure, "PEG" refers to "polyethylene glycol" which is a polymer composed of ethylene oxide repeating units. "Methoxy PEG" means monomethoxy-polyethylene glycol (MeO-PEG), which has methoxy and hydroxyl terminal groups and ethylene oxide repeating units. As used herein, the number of ethylene oxide repeating units is depicted as an individual number (e.g., "PEG1", "PEG2", "PEG3", etc.) or a range of the number of repeating units (e.g., "PEG1-10", "PEG3-10", "PEG2-8", etc.). When used herein, a numerical range such as "1 to 10" refers to each integer in the given range, e.g., "1 to 10 ethylene oxide units" means that the compound may have 1 ethylene oxide unit, 2 ethylene oxide units, 3 ethylene oxide units, etc., up to and including 10 ethylene oxide units. In accordance with aspects of the present disclosure, the PEG of the diglycidyl ether diphenolic ester is any one of PEG with 1 to 10 ethylene oxide units, i.e., PEG1 to PEG10. Preferably, the PEG of the diglycidyl ether diphenolic ester is PEG having 1 ethylene oxide unit, i.e., PEG1. In some embodiments, PEG in "diglycidyl ether diphenolic methoxy PEG" has 1 to 10 ethylene oxide units (i.e., PEG1 to PEG10). In some embodiments, PEG in "diglycidyl ether diphenolic methoxy PEG" is PEG1.

The wall of the microcapsule of the present disclosure can be prepared by interfacial polymerization of the biobased epoxide with a polyamine in the absence of an isocyanate and/or polyisocyanate. As used herein, interfacial polymerization refers to a type of step-growth polymerization in which polymerization occurs at the interface between two immiscible phases (generally two liquids such as oil phase and aqueous phase), resulting in a polymer that is constrained to the interface.

A polyamine refers to a chemical compound or polymer or biopolymer (e.g., proteins and polysaccharides) that have more than one amine functional group that is primary or secondary amine. The chemical compound or polymer may contain additional functional groups such as hydroxyl, carboxylate, etc. Ideally, interfacial polymerization is carried out with a polyamine. Examples of suitable polyamines include, but are not limited to, ethylene diamine (EDA), hexamethylene diamine (HMDA), diethylene triamine (DETA), dihydrazide, dipropylenetriamine (norspermidine), triethylene tetramine (TETA), tetraethylene pentamine (TEPA), and combinations thereof. In some embodiments, the dihydrazide is selected from the group consisting of adipic acid dihydrazide, isophthalic dihydrazide, terephthalic dihydrazide, suberic acid dihydrazide, sebacic dihydrazide, malonic acid dihydrazide, 2-hydroxypropane-1,2,3-tricarbohydrazide, and combinations thereof. In some embodiments, the dihydrazide is adipic acid dihydrazide and/or suberic acid dihydrazide. Examples of biopolymers that have more than one amine functional groups include, but are not limited to, chitosan, chitosan oligosaccharide, guanidine carbonate, ε-poly(L-lysine), α-poly(L-lysine), L-lysine containing peptides, L-lysine containing proteins, amine functionalized cellulose and guar, amidated pectin, gelatin, pea proteins, whey protein, rice protein, potato protein, and combinations thereof.

Chitosan oligosaccharide (COS) is an oligomer of chitosan. Like chitosan, the chemical structure of COS is a linear binary copolymer composed of β-1,4-linked 2-acetamido-2-deoxy-β-D-glucopyranose (GlcNAc) and 2-amino-2-deoxy-β-D-glucopyranose (GlcN). COS can be prepared from the deacetylation and hydrolysis of chitin, which is commonly found in the exoskeletons of arthropods and insects and the cell walls of fungi. Preferably, the COS used in the preparation of a microcapsule shell of the present disclosure has an average molecular weight of less than or equal to 20,000 Da.

In some embodiments, the biobased epoxide is polymerized by interfacial polymerization with hexamethylene diamine (HMDA) and COS. In some embodiments, the biobased epoxide is polymerized by interfacial polymerization with hexamethylene diamine (HMDA) and guanidine carbonate. In some embodiments, the weight ratio of HMDA to COS is from 10:1 to 1.5:1 and preferably from 2:1 to 1.5:1 or from 10:1 to 2:1. In some embodiments, the weight ratio of HMDA to guanidine carbonate is from 10:1 to 1.5:1 and preferably from 2:1 to 1.5:1 or from 10:1 to 2:1.

In certain aspects, the biobased epoxide is polymerized by interfacial polymerization with a polyamine in the presence of at least one emulsifier or surfactant. Commercially available emulsifiers include, but are not limited to, sulfonated naphthalene-formaldehyde condensates sold under the tradename MORWET® D425 (sodium salt of alkylnaphthalenesulfonate formaldehyde condensate, Akzo Nobel, Fort Worth, TX), partially hydrolyzed polyvinyl alcohols sold under the tradenames MOWIOL®, e.g., MOWIOL® 3-83 (Air Products), or SELVOL® 203 (Sekisui), polyvinyl alcohols such as Ultalux FP, Ultalux FA, Ultalux AD, OKS-8089 (Sourus), ethylene oxide-propylene oxide block copolymers or poloxamers sold under the tradenames PLURONIC®, SYNPERONIC® or PLURACARE® materials (BASF), sulfonated polystyrenes sold under the tradename FLEXAN® II (Akzo Nobel), ethylene-maleic anhydride polymers sold under the tradename ZEMAC® (Vertellus Specialties Inc.), copolymer of acrylamide and acrylamidopropyltrimonium chloride sold under the tradename SALCARE® SC 60 (BASF), polyquaternium series such as Polyquaternium 11, gum Arabic, a naturally sourced complex mixture of glycoproteins and polysaccharides that is water soluble, edible, and used in food industries as a stabilizer, sophorolipid butyl ester (SLBE), a non-ionic low-molecular-weight naturally derived glycolipid that proved to be an excellent stabilizer for oil-water emulsions, polyvinyl pyrrolidone (PVP) and PQ-11 cosurfactant system, and combinations thereof. In certain aspects, the emulsifier is selected from the group consisting of gum Arabic, polyvinyl alcohol, sophorolipid butyl ester, polyvinyl pyrrolidone, polyquaternium-11, and combinations thereof.

Encapsulation Methods

As demonstrated herein, a biobased epoxide polymerized by interfacial polymerization with a polyamine produces microcapsules with strongly cross-linked epoxy walls, low interparticle aggregation and high fragrance oil encapsulation efficiency. As such, the microcapsules of the present disclosure provide an alternative for isocyanate and formaldehyde approaches for oil encapsulation. Thus, in certain aspects, the microcapsule shell does not comprise isocyanate, formaldehyde, and/or polymer formed with isocyanate and formaldehyde.

This present disclosure also provides methods for producing core-shell microcapsule compositions, which have better biodegradability comparing with previous synthetic microcapsules (e.g., melamine formaldehyde and polyurea based capsules). Generally, the present disclosure provides a method for preparing a core-shell microcapsule composition by emulsifying an active material with at least one biobased epoxide to form an emulsion; adding a polyamine to the emulsion; and providing a condition sufficient to induce interfacial polymerization in the emulsion to form a slurry that comprises core-shell microcapsules each having a microcapsule shell encapsulating a microcapsule core. In some embodiments, the emulsion is an oil-in-water emulsion, and the slurry is an aqueous slurry.

In some aspects, the present disclosure provides a method for preparing a core-shell microcapsule composition. The method comprises: (a) emulsifying an active material with at least one biobased epoxide to form an emulsion, wherein the at least one biobased epoxide is diglycidyl ether diphenolic ester, preferably the at least one biobased epoxide is selected from the group consisting of diglycidyl ether diphenolic methyl ester, diglycidyl ether diphenolic ethyl ester, diglycidyl ether diphenolic propyl ester, diglycidyl ether diphenolic butyl ester, diglycidyl ether diphenolic pentyl ester, diglycidyl ether diphenolic methoxy PEG, and combinations thereof, wherein the PEG is a PEG having 1 to 10 ethylene oxide units, preferably the PEG has 1 ethylene oxide unit; (b) adding a polyamine to the emulsion, preferably the polyamine is selected from the group consisting of hexamethylene diamine (HMDA), ethylene diamine (EDA), diethylene triamine (DETA), dihydrazide, dipropylenetriamine (norspermidine), triethylene tetramine (TETA), tetraethylene pentamine (TEPA), chitosan oligosaccharide (COS), guanidine carbonate, ε-poly(L-lysine), α-poly(L-lysine), L-lysine containing peptides, L-lysine containing proteins, gelatin, and combinations thereof, preferably the COS has an average molecular weight of less than or equal to 20,000 Da; and (c) providing a condition sufficient to induce interfacial polymerization in the emulsion to form a slurry that comprises core-shell microcapsules each having a microcapsule shell encapsulating a microcapsule core, thereby obtaining the core-shell microcapsule composition.

In some aspects, at least one emulsifier is used to help forming the emulsion, that is, the emulsion comprises at least one emulsifier. In some embodiments, the at least one emulsifier is selected from the group consisting of gum Arabic, polyvinyl alcohol (PVA), sophorolipid butyl ester (SLBE), polyvinyl pyrrolidone (PVP), polyquaternium-11 (PQ-11), and combinations thereof.

In some embodiments, the microcapsules of the present disclosure are prepared at a temperature of no more than 200° C., preferably no more than 150° C., preferably no more than 90° C., or preferably no more than 80° C. In some embodiments, the microcapsules are prepared at a temperature in the range of from 25° C. to 90° C. (e.g., from 75° C. to 85° C.) for 1 hour to 48 hours (e.g., 2 hours to 5 hours, or 3 hours to 5 hours). Preferably, the microcapsules are prepared at a temperature of about 80° C. for about 4 hours. More preferably, the microcapsules are prepared at a temperature of about 80° C. for up to 24 hours.

The microcapsules of the present disclosure preferably has a mean diameter particle size in the range of from 5 μm to 100 μm, preferably in the range of from 10 μm to 75 μm, or more preferably in the range of from 10 μm to 50 μm. The microcapsules produced by the method of the present disclosure are single microcapsules (i.e., not agglomerated), and can have a size distribution that is narrow, broad, or multi-modal.

In so far as the microcapsules of the present disclosure are prepared with a biobased epoxide, the microcapsules provide a biodegradable alternative to isocyanate or melamine-formaldehyde microcapsule systems thus contributing to human health and the environment. Accordingly, other aspects of the present disclosure provide for the use of a biobased epoxide for increasing the degree of biodegradability of a microcapsule shell in a core-shell microcapsule composition and a method for increasing the degree of biodegradability of a core-shell microcapsule by incorporating at least one biobased epoxide into the shell of the core-shell microcapsule through interfacial polymerization of the biobased epoxide with a polyamine including a biopolymer having amine functional groups.

In some embodiments, the biobased epoxide is a diglycidyl ether diphenolic ester. In some embodiments, the biobased epoxide is selected from the group consisting of diglycidyl ether diphenolic (DGEDP) methyl ester, diglycidyl ether diphenolic ethyl ester, diglycidyl ether diphenolic propyl ester, diglycidyl ether diphenolic butyl ester, diglycidyl ether diphenolic pentyl ester, diglycidyl ether diphenolic methoxy PEG, and combinations thereof, wherein the PEG is a PEG having 1 to 10 ethylene oxide units. In some embodiments, the PEG has 1 ethylene oxide unit. In some embodiments, the polyamine is selected from the group consisting of hexamethylene diamine (HMDA), ethylene diamine (EDA), diethylene triamine (DETA), dihydrazide, dipropylenetriamine (norspermidine), triethylene tetramine (TETA), tetraethylene pentamine (TEPA), chitosan oligosaccharide (COS), guanidine carbonate, ε-poly(L-lysine), α-poly(L-lysine), L-lysine containing peptides, L-lysine containing proteins, gelatin, and combinations thereof. In some embodiments, the polyamine is selected from the group consisting of COS, ε-poly(L-lysine), α-poly(L-lysine), L-lysine containing peptides, L-lysine containing proteins, gelatin, and combinations thereof. In some embodiments, the COS has an average molecular weight of less than or equal to 20,000 Da. In some embodiments, the interfacial polymerization is carried out in the presence of at least one emulsifier. In some embodiments, the at least one emulsifier is selected from the group consisting of gum Arabic, polyvinyl alcohol (PVA), sophorolipid butyl ester (SLBE), polyvinyl pyrrolidone (PVP), polyquaternium-11 (PQ-11), and combinations thereof.

Adjunct Core Materials. In addition to the active materials, the present disclosure also provides for the incorporation of adjunct materials including solvents, emollients, and core modifier materials in the core encapsulated by the capsule wall. Other adjunct materials may include nanoscale solid particulate materials, polymeric core modifiers, solubility modifiers, density modifiers, stabilizers, humectants, viscosity modifiers, pH modifiers, or a combination thereof. These modifiers can be present in the wall or core of the capsules, or outside the capsules in delivery system. Preferably, they are in the core as a core modifier.

The one or more adjunct material can be added in the amount of from 0.01% to 25% (e.g., from 0.5% to 10%) by weight of the capsule.

Examples of suitable adjunct materials include those described in WO 2016/049456 and US 2016/0158121.

Deposition Aids. A capsule deposition aid from 0.01% to 25%, more preferably from 5% to 20% by weight of the capsule can be included in the core-shell microcapsule composition. The capsule deposition aid can be added during the preparation of the capsules, or can be added after the capsules have been made.

These deposition aids are used to aid in deposition of capsules to surfaces such as fabric. These include anionic, cationic, non-ionic, or amphoteric water-soluble polymers. Suitable deposition aids include polyquaternium-4, polyquaternium-5, polyquaternium-6, polyquaternium-7, polyquaternium-10, polyquaternium-16, polyquaternium-22, polyquaternium-24, polyquaternium-28, polyquaternium-39, polyquaternium-44, polyquaternium-46, polyquaternium-47, polyquaternium-53, polyquaternium-55, polyquaternium-67, polyquaternium-68, polyquaternium-69, polyquaternium-73, polyquaternium-74, polyquaternium-77, polyquaternium-78, polyquaternium-79, polyquaternium-80, polyquaternium-81, polyquaternium-82, polyquaternium-86, polyquaternium-88, polyquaternium-101, polyvinylamine, polyethyleneimine, polyvinylamine and vinylformamide copolymer, an acrylamidopropyltrimonium chloride/acrylamide copolymer, a methacrylamidopropyltrimonium chloride/acrylamide copolymer, polymer comprising units derived from polyethylene glycol and terephthalate, polyester, polymer derivable from dicarboxylic acids and polyols, or a combination thereof. Other suitable deposition aids include those described in WO 2016/049456, pages 13-27. Additional deposition aids are described in US 2013/0330292, US 2013/0337023, and US 2014/0017278.

Rheology Modifiers. One or more rheology modifiers or viscosity control agents can be added to the microcapsule composition to achieve a desired viscosity of the composition so that the microcapsule is dispersed in the composition for a pro-longed time period. In some embodiments, during capsule preparation, the rheology modifier is added prior to the emulsification of the aqueous phase and oil phase and is typically disperses homogeneously in the microcapsule slurry and outside of the microcapsule wall of the microcapsules in the composition of the present disclosure. In other embodiments, during capsule preparation, the rheology modifier is added after the emulsification of the aqueous phase and oil phase. Suitable rheology modifiers include an acrylate copolymer, a cationic acrylamide copolymer, a polysaccharide, or a combination thereof.

Commercially available acrylate copolymers include those under the tradename ACULYN® (from Dow Chemical Company) such as ACULYN® 22 (a copolymer of acrylates and steareth-20 methacrylate), ACULYN® 28 (a copolymer of acrylate and beheneth-25 methacrylate), ACULYN® 33 (a copolymer of acrylic acid and acrylate), ACULYN® 38 (a cross polymer of acrylate and vinyl neodecanoate), and ACULYN® 88 (a cross polymer of acrylate and steareth-20 methacrylate). Particularly useful acrylate copolymers are anionic acrylate copolymer such as ACULYN® 33, an alkali-soluble anionic acrylic polymer emulsion (ASE), which is synthesized from acrylic acid and acrylate comonomers through emulsion polymerization. Acrylate copolymers sold under the tradename CARBOPOL® are also suitable for use in the present disclosure. Examples are CARBOPOL® ETD 2020 polymer (a cross polymer of acrylate and $C_{10}$-$C_{30}$ alkyl acrylate), CARBOPOL® ETD 2691, and CARBOPOL® ETD 2623 (a crosslinked acrylate copolymer).

Polysaccharides are another class of agents suitable as rheology modifiers. In certain aspects, polysaccharides of use as rheology modifiers include starches, pectin, and vegetable gums such as, guar gum, locust bean gum, and xanthan gum, e.g., xanthan gum sold under the tradename KELTROL® T (80-mesh food-grade), commercially available from CP Kelco, Atlanta, GA). Preferably, the at least one rheology modifier is a xanthan gum.

Preservatives. One or more preservatives can be added to the microcapsule composition to prevent damage or inadvertent growth of microorganisms for a specific period of time thereby increasing shelf life. The preservative can be any organic preservative that does not cause damage to the microcapsule composition. Suitable water-soluble preservatives include organic sulfur compounds, halogenated compounds, cyclic organic nitrogen compounds, low molecular weight aldehydes, parabens, propanediol materials, isothiazolinone, quaternary compounds, and benzoates. Examples include low molecular weight alcohols, dehydroacetic acids, phenyl and phenoxy compounds, or a combination thereof.

A non-limiting example of commercially available water-soluble preservative is a mixture of about 77% 5-chloro-2-methyl-4-isothiazolin-3-one and 23% 2-methyl-4-isothiazolin-3-one. Additional antibacterial preservatives include a 1.5% aqueous solution under the tradename KATHON® CG of Rohm &Haas; 5-bromo available under the tradename BRONIDOX L® of Henkel; 2-bromo-2-nitro-1,3-propanediol available under the tradename BRONOPOL® of Inorex; 1,1'-Hexamethylenebis (5-(p-chlorophenyl) biguanide) and salts thereof, such as acetates and digluconates; 1,3-bis (hydroxy) available under the tradename GLYDANT PLUS® from Ronza; glutaraldehyde; ICI Polyaminopropylbiguanide; dehydroacetic acid; and 1,2-Benzisothiazolin-3-one sold under the tradename PROXEL® GXL.

Microcapsule Delivery System Formulations

The microcapsule composition can be formulated into a capsule delivery system (e.g., a microcapsule composition) for use in consumer products.

The capsule delivery system can be a microcapsule slurry suspended in an external solvent (e.g., water, ethanol, or a combination thereof), wherein the capsule is present at a level of from 0.1% to 80% (e.g., 70-75%, 40-55%, 50-90%, 1% to 65%, and 5% to 45%) by weight of the capsule delivery system.

Alternatively, or in addition to, the capsule and its slurry prepared in accordance with the present disclosure is subsequently purified. See US 2014/0017287. Purification can be achieved by washing the capsule slurry with water until a neutral pH is obtained.

Additional Components. The capsule delivery system can optionally contain one or more other delivery system such as polymer-assisted delivery compositions (see U.S. Pat. No. 8,187,580), fiber-assisted delivery compositions (US 2010/0305021), cyclodextrin host guest complexes (U.S. Pat. No. 6,287,603 and US 2002/0019369), pro-fragrances (WO 2000/072816 and EP 0922084), or a combination thereof. The capsule delivery system can also contain one or more (e.g., two, three, four, five or six more) different capsules including different capsules of the present disclosure and other capsules such as such as aminoplasts, hydrogel, sol-gel, polyurea/polyurethane capsules, and melamine formaldehyde capsules. More exemplary delivery systems that can be incorporated are coacervate capsules (see WO 2004/022221) and cyclodextrin delivery systems (see WO 2013/109798 and US 2011/03085560).

Any compound, polymer, or agent discussed above can be the compound, polymer, or agent itself as shown above, or its salt, precursor, hydrate, or solvate.

Certain compounds, polymers, and agents have one or more stereocenters, each of which can be in the R or S configuration, or a combination thereof. Further, some compounds, polymers, and agents possess one or more double bonds wherein each double bond exists in the E (trans) or Z (cis) configuration, or a combination thereof. The compounds, polymers, and agents include all possible configurational stereoisomeric, regioisomeric, diastereomeric, enantiomeric, and epimeric forms as well as a combination thereof. As such, lysine used herein includes L-lysine, D-lysine, L-lysine monohydrochloride, D-lysine monohydrochloride, lysine carbonate, and so on. Similarly, arginine includes L-arginine, D-arginine, L-arginine monohydrochloride, D-arginine monohydrochloride, arginine carbonate, arginine monohydrate, etc. Guanidine includes guanidine hydrochloride, guanidine carbonate, guanidine thiocyanate, and other guanidine salts including their hydrates. Ornithine include L-ornithine and its salts/hydrates (e.g., monohydrochloride) and D-ornithine and its salts/hydrates (e.g., monohydrochloride).

Applications

The delivery systems of the present disclosure are well-suited for use, without limitation, in laundry detergent, a liquid laundry detergent, a powder laundry detergent, a tablet laundry detergent, a laundry detergent bar, a laundry detergent cream, a hand wash laundry detergent, a fabric conditioner or softener, a fabric refresher, a scent booster, a shampoo, a hair conditioner, a bar soap, a shower gel, a body wash, an antiperspirant, a body spray, a body mist, a lotion, a candle or a textile.

More specifically, the microcapsules of the present disclosure are use in the following products:

A) Fabric Care Products such as Rinse Conditioners (containing 1 to 30 weight % of a fabric conditioning active), Fabric Liquid Conditioners (containing 1 to 30 weight % of a fabric conditioning active), Tumble Drier Sheets, Fabric Refreshers, Fabric Refresher Sprays, Ironing Liquids, and Fabric Softener Systems such as those described in U.S. Pat. Nos. 6,335,315, 5,674,832, 5,759,990, 5,877,145, 5,574,179, 5,562,849, 5,545,350, 5,545,340, 5,411,671, 5,403,499, 5,288,417, 4,767,547 and 4,424,134.

Liquid fabric softeners/fresheners contain at least one fabric softening agent present, preferably at a concentration of 1 to 30% (e.g., 4% to 20%, 4% to 10%, and 8% to 15%) by weight of the liquid fabric softener/freshener. The ratio between the active material and the fabric softening agent can be 1:500 to 1:2 (e.g., 1:250 to 1:4 and 1:100 to 1:8). As an illustration, when the fabric softening agent is 5% by weight of the fabric softener, the active material is 0.01% to 2.5%, preferably 0.02% to 1.25% and more preferably 0.1% to 0.63%. As another example, when the fabric softening agent is 20% by weight of the fabric softener, the active material is 0.04% to 10%, preferably 0.08% to 5% and more preferably 0.4% to 2.5%. The active material is a fragrance, malodor counteractant or a combination thereof. The liquid fabric softener can have 0.15% to 15% of capsules (e.g., 0.5% to 10%, 0.7% to 5%, and 1% to 3%). When including capsules at these levels, the neat oil equivalent (NOE) in the softener is 0.05% to 5% (e.g., 0.15% to 3.2%, 0.25% to 2%, and 0.3% to 1%).

Suitable fabric softening agents include cationic surfactants. Non-limiting examples are quaternary ammonium compounds (QAC) such as alkylated quaternary ammonium compounds, ring or cyclic quaternary ammonium compounds, aromatic quaternary ammonium compounds, diquaternary ammonium compounds, alkoxylated quaternary ammonium compounds, amidoamine quaternary ammonium compounds, ester quaternary ammonium compounds, or a combination thereof.

Fabric softening product includes an aqueous QAC which are characterized by:

a) The viscosity of the final product ranges from 5 to 300 cps @ 106 s-1, preferable 20 to 150 cps;

b) The level of QAC ranges 0.5 to 20 wt %, preferably from 1 to 16 wt %, more preferably 6 to 12 wt % softening active. The preferred, typical cationic fabric softening components include water-insoluble quaternary-ammonium fabric softeners, the most commonly used having been di-long alkyl chain ammonium chloride or methyl sulfate. Preferred cationic softeners include but not limited to the following:

a. rapidly biodegradable quaternary ammonium compounds which contain 1 or more ester bonds situated between the quaternary-ammonium group and the long alkyl chain (e.g., TEA ester quats, DEEDMAC and HEQ);

b. Non-Ester quaternary ammonium compounds (e.g., ditallow dimethylammonium chloride (DTDMAC); dihydrogenated tallow dimethylammonium chloride; dihydrogenated tallow dimethylammonium methylsulfate; distearyl dimethylammonium chloride; dioleyl dimethylammonium chloride; dipalmityl hydroxyethyl methylammonium chloride; stearyl benzyl dimethylammonium chloride; tallow trimethylammonium chloride; hydrogenated tallow trimethylammonium chloride; C12-14 alkyl hydroxyethyl dimethylammonium chloride; C12-18 alkyl dihydroxyethyl methylammonium chloride; di(stearoyloxyethyl) dimethylammonium chloride (DSOEDMAC); di(tallowoyloxyethyl) dimethylammonium chloride; ditallow imidazolinium methylsulfate; 1-(2-tallowylamidoethyl)-2-tallowyl imidazolinium methylsulfate.

A first group of quaternary ammonium compounds (QACs) suitable for use according to the present disclosure is represented by formula (I):

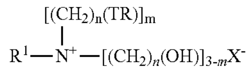

(I)

wherein each R is independently selected from a $C_1$-$C_{35}$ alkyl or alkenyl group; $R^1$ represents a $C_1$-$C_4$ alkyl, $C_2$-$C_4$ alkenyl or a $C_1$-$C_4$ hydroxyalkyl group; T is generally O—CO (i.e., an ester group bound to R via its carbon atom), but may alternatively be CO—O (i.e., an ester group bound to R via its oxygen atom); n is a number selected from 1 to 4; m is a number selected from 1, 2, or 3; and X is an anionic counter-ion, such as a halide or alkyl sulphate, e.g., chloride or methylsulphate. Di-esters variants of formula (I) (i.e., m=2) are preferred and typically have mono- and tri-ester analogues associated with them.

Especially preferred agents are preparations which are rich in the di-esters of triethanolammonium methylsulfate, otherwise referred to as "TEA ester quats". Commercial examples include STEPANTEX® UL85, ex Stepan, Prapagen™ TQL, ex Clariant, and Tetranyl™ AHT-1, ex Kao, (both di-[hardened tallow ester] of triethanolammonium methylsulphate), AT-1 (di-[tallow ester] of triethanolammonium methylsulphate), and L5/90 (di-[palm ester] of triethanolammonium methylsulphate), both ex Kao, and REWOQUAT® WE15 (a di-ester of triethanolammonium methylsulphate having fatty acyl residues deriving from C10-$C_{20}$ and $C_{16}$-$C_{18}$ unsaturated fatty acids), ex Evonik.

Also suitable are soft quaternary ammonium actives such as STEPANTEX® VK90, STEPANTEX® VT90, SP88 (ex-Stepan), Prapagen™ TQ (ex-Clariant), DEHYQUART® AU-57 (ex-Cognis), REWOQUAT® WE18 (ex-Degussa) and Tetranyl™ L190 P, Tetranyl™ L190 SP and Tetranyl™ L190 S (all ex-Kao).

A second group of QACs suitable for use according to the present disclosure is represented by formula (II):

$$(R^1)_2—N^+—[(CH_2)_n\text{-}T\text{-}R^2]_2X^- \quad \text{(II)}$$

wherein each $R^1$ group is independently selected from $C_1$-$C_4$ alkyl, or $C_2$-$C_4$ alkenyl groups; and wherein each $R_2$ group is independently selected from $C_8$-$C_{28}$ alkyl or alkenyl groups; and n, T, and X— are as defined above. Preferred materials of this second group include bis(2tallwoyloxyethyl)dimethyl ammonium chloride and hardened versions thereof.

A third group of QACs suitable for use according to the present disclosure is represented by formula (III):

(III)

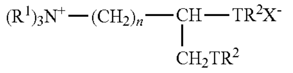

wherein each $R^1$ group is independently selected from $C_1$-$C_4$ alkyl, hydroxyalkyl or $C_2$-$C_4$ alkenyl groups; and wherein each $R^2$ group is independently selected from $C_8$-$C_{28}$ alkyl or alkenyl groups; and wherein n, T, and X are as defined above. Preferred materials of this second group include 1,2 bis[tallowoyloxy]-3-trimethylammonium propane chloride, 1,2 bis[hardened tallowoyloxy]-3-trimethylammonium propane chloride, 1,2-bis[oleoyloxy]-3 trimethylammonium propane chloride, and 1,2 bis[stearoyloxy]-3-trimethylammonium propane chloride. Such materials are described in U.S. Pat. No. 4,137,180 (Lever Brothers). Preferably, these materials also comprise an amount of the corresponding mono-ester.

Non-ester quaternary ammonium compounds may be a non-ester quaternary ammonium material represented by formula (IV):

(IV)

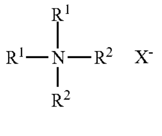

wherein each $R^1$ group is independently selected from $C_1$-$C_4$ alkyl, hydroxyalkyl or $C_2$-$C_4$ alkenyl groups; each $R^2$ group is independently selected from $C_5$-$C_{28}$ alkyl or alkenyl groups, and X is as defined above.

The fabric conditioner composition may optionally contain a non-cationic softening material, which is preferably an oily sugar derivative. An oily sugar derivative is a liquid or soft solid derivative of a cyclic polyol (CPE) or of a reduced saccharide (RSE), said derivative resulting from 35 to 100% of the hydroxyl groups in said polyol or in said saccharide being esterified or etherified. The derivative has two or more ester or ether groups independently attached to a $C_8$-$C_{22}$ alkyl or alkenyl chain. Advantageously, the CPE or RSE does not have any substantial crystalline character at 20° C. Instead, it is preferably in a liquid or soft solid state as herein defined at 20° C. The liquid or soft solid (as hereinafter defined) CPEs or RSEs suitable for use according to the present disclosure result from 35 to 100% of the hydroxyl groups of the starting cyclic polyol or reduced saccharide being esterified or etherified with groups such that the CPEs or RSEs are in the required liquid or soft solid state. These groups typically contain unsaturation, branching or mixed chain lengths. Typically, the CPEs or RSEs have 3 or more ester or ether groups or mixtures thereof, for example 3 to 8, especially 3 to 5. It is preferred if two or more of the ester or ether groups of the CPE or RSE are independently of one another attached to a $C_5$ to $C_{22}$ alkyl or alkenyl chain. The $C_5$ to $C_{22}$ alkyl or alkenyl groups may be branched or linear carbon chains.

Co-softeners. Co-softeners, also referred to as co-softeners and fatty complexing agents may be used in fabric conditioner composition of the present disclosure. When employed, they are typically present at from 0.1 to 20% and particularly at from 0.1 to 5%, based on the total weight of the composition. Preferred co-softeners include fatty alcohols, fatty esters, and fatty N-oxides. Fatty esters that may be employed include fatty monoesters, such as glycerol monostearate, fatty sugar esters, such as those disclosed WO 01/46361 (Unilever).

The compositions of the present disclosure may comprise a co-actives. Especially suitable fatty complexing agents include fatty alcohols and fatty acids. Of these, fatty alcohols are most preferred. Without being bound by theory it is believed that the fatty complexing material improves the viscosity profile of the composition by complexing with mono-ester component of the fabric conditioner material thereby providing a composition which has relatively higher levels of di-ester and tri-ester linked components. The di-ester and tri-ester linked components are more stable and do not affect initial viscosity as detrimentally as the mono-ester component. It is also believed that the higher levels of mono-ester linked component present in compositions comprising quaternary ammonium materials based on TEA may destabilize the composition through depletion flocculation. By using the co-active material to complex with the mono-ester linked component, depletion flocculation is significantly reduced. In other words, the co-active at the increased levels, as required by the present disclosure, "neutralizes" the mono-ester linked component of the quaternary ammonium material. This in situ di-ester generation from mono-ester and fatty alcohol also improves the softening of the composition.

Preferred fatty acids include hardened tallow fatty acid (available under the trade name PRISTERENE®, ex Croda). Preferred fatty alcohols include hardened tallow alcohol (available under the trade names STENOL® and HYDRENOL®, ex BASF and LAUREX® CS, ex Huntsman). The fatty complexing agent may be preferably present in an amount greater than 0.1 to 5% by weight based on the total weight of the composition. More preferably, the fatty component may be present in an amount of from 0.2 to 4%. The weight ratio of the mono-ester component of the quaternary ammonium fabric softening material to the fatty complexing agent is preferably from 5:1 to 1:5, more preferably 4:1 to 1:4, most preferably 3:1 to 1:3, e.g., 2:1 to 1:2.

Fatty Acids. The fabric conditioner composition may further comprise a fatty acid compound. Suitable fatty acids include those containing from 10 to 25, preferably from 12 to 25 total carbon atoms, with the fatty moiety containing from 10 to 22, preferably from 16 to 22, carbon atoms. The level of unsaturation of the tallow chain can be measured by the Iodine Value (IV) of the corresponding fatty acid, which in the present case should preferably be in the range of from 5 to 100, more preferably in the range of from 0 to 25. Specific examples of fatty acid compounds suitable for use in the aqueous fabric softening compositions herein include compounds selected from lauric acid, myristic acid, palmitic acid, stearic acid, arachidic acid, behenic acid, oleic acid, coconut fatty acid, tallow fatty acid, partially hydrogenated tallow fatty acid and mixtures thereof. A most preferred fatty acid compound is tallow fatty acid with an Iodine Value (IV) of 18. The fatty acids, when present, will preferably be in a weight ratio of said biodegradable fabric softening agents to said fatty acid compounds of from 25:1 to 6.5:1, more preferably from 20:1 to 10:1 and most preferably from 20:1 to 15:1.

Rheology Modifiers. The compositions may further comprise a rheology modifiers. Rheology modifiers particularly useful in the compositions of the present disclosure include those described in WO2010/078959 (SNF S.A.S.). These are crosslinked water swellable cationic copolymers of at least one cationic monomer and optionally other non-ionic and/or anionic monomers. Preferred polymers of this type are copolymers of acrylamide and methacrylate. Most preferred are copolymers of acrylamide and trimethylaminoethylacrylate chloride. The composition may comprise one cross-linked water swellable cationic copolymer.

In one embodiment of the present disclosure, it may be preferred that the composition comprises at least two different crosslinked water swellable cationic copolymers. Preferred polymers comprise less than 25% of water soluble polymers by weight of the total polymer, preferably less than 20%, and most preferably less than 15%, and a cross-linking agent concentration of from 500 ppm to 5000 ppm by weight relative to the polymer, preferably from 750 ppm to 5000 ppm by weight, more preferably from 1000 to 4500 ppm by weight as determined by a suitable metering method such as the following method described on page 4 of patent EP 2373773 B 1. Suitable cationic monomers are selected from the group consisting of the following monomers and derivatives and their quaternary or acid salts: dimethylaminopropylmethacrylamide, dimethylaminopropylacrylamide, diallylamine, methyldiallylamine, dialkylaminoalkyl-acrylates and methacrylates, dialkylaminoalkylacrylamides or -methacrylamides.

Following is a non-restrictive list of monomers performing a non-ionic function: acrylamide, methacrylamide, N-Alkyl acrylamide, N-vinyl pyrrolidone, N-vinyl formamide, N-vinyl acetamide, vinylacetate, vinyl alcohol, acrylate esters, and allyl alcohol.

Following is a non-restrictive list of monomers performing an anionic function: acrylic acid, methacrylic acid, itaconic acid, crotonic acid, maleic acid, fumaric acid, as well as monomers performing a sulfonic acid or phosphonic acid functions, such as 2-acrylamido-2-methyl propane sulfonic acid (ATBS) etc.

The monomers may also contain hydrophobic groups. Following is a non-restrictive list of cross-linking agents: methylene bisacrylamide (MBA), ethylene glycol diacrylate, polyethylene glycol dimethacrylate, diacrylamide, triallylamine, cyanomethylacrylate, vinyl oxyethylacrylate or methacrylate and formaldehyde, glyoxal, compounds of the glycidyl ether type such as ethyleneglycol diglycidyl ether, or the epoxides or any other means familiar to the expert permitting cross-linking.

The cross-linking rate preferably ranges from 800 to 5000 ppm (on the basis of methylene bisacrylamide) by weight relative to the polymer or equivalent cross-linking with a cross-linking agent of different efficiency. As described in US 2002/0132749, the degree of nonlinearity can additionally be controlled by the inclusion of chain transfer agents (such as isopropyl alcohol, sodium hypophosphite, mercaptoethanol) in the polymerization mixture in order to control the polymeric chain's length and the cross-linking density. The amount of polymer used in the compositions of the present disclosure is suitably from 0.001 to 0.5 wt %, preferably from 0.005 to 0.4 wt %, more preferably from 0.05 to 0.35 wt % and most preferably from 0.1 to 0.25 wt %, by weight of the total composition. An example of a preferred polymer is FLOSOFT® 270LS ex SNF and FLOSOFT® 222 ex SNF.

Silicone. The compositions of the present disclosure may further contain a silicone based fabric softening agent. Preferably the fabric softening silicone is a polydimethylsiloxane. The fabric softening silicones include but are not limited to 1) non-functionalized silicones such as polydimethylsiloxane (PDMS) or alkyl (or alkoxy) functional silicones; 2) functionalized silicones or copolymers with one or more different types of functional groups such as amino, phenyl, polyether, acrylate, silicon hydride, carboxylic acid, quaternized nitrogen, etc. Suitable silicones may be selected from polydialkylsiloxanes, preferably polydimethylsiloxane more preferably amino functionalised silicones; anionic silicones and carboxyl functionalized silicone. An amino silicone that may also be used, for example, Arristan 64, ex CHT or Wacker CT45E, ex Wacker.

In terms of silicone emulsions, the particle size can be in the range from about 1 nm to 100 microns and preferably from about 10 nm to about 10 microns including microemulsions (<150 nm), standard emulsions (about 200 nm to about 500 nm) and macroemulsions (about 1 micron to about 20 microns).

Non-ionic surfactants. The compositions may further comprise a nonionic surfactant. Typically, these can be included for the purpose of stabilizing the compositions. Suitable nonionic surfactants include addition products of ethylene oxide with fatty alcohols, fatty acids, and fatty amines. Any of the alkoxylated materials of the particular type described hereinafter can be used as the nonionic surfactant. Suitable surfactants are substantially water soluble surfactants of the general formula (V): R—Y—$(C_2H_4O)z$-$CH_2$—$CH_2$—OH (V) where R is selected from the group consisting of primary, secondary and branched chain alkyl and/or acyl hydrocarbyl groups; primary, secondary and branched chain alkenyl hydrocarbyl groups; and primary, secondary and branched chain alkenyl-substituted phenolic hydrocarbyl groups; the hydrocarbyl groups having a chain length of from 8 to about 25, preferably 10 to 20, e.g., 14 to 18 carbon atoms. In the general formula for the ethoxylated nonionic surfactant, Y is typically: —O—, —C(O)O—, —C(O)N(R)— or —C(O)N(R)R in which R has the meaning given above for formula (V), or can be hydrogen; and Z is at least about 8, preferably at least about 10 or 11.

Preferably the nonionic surfactant has an HLB of from about 7 to about 20, more preferably from 10 to 18, e.g., 12 to 16. GENAPOL® C200 (Clariant) based on coco chain and 20 EO groups is an example of a suitable nonionic surfactant. If present, the nonionic surfactant is present in an amount from 0.01 to 10%, more preferably 0.1 to 5 by weight, based on the total weight of the composition. LUTENSOL® AT25 (BASF) based on coco chain and 25 EO groups is an example of a suitable non-ionic surfactant. Other suitable surfactants include RENEX® 36 (Trideceth-6), ex Croda; TERGITOL® 15-S3, ex Dow Chemical Co.; Dihydrol LT7, ex Thai Ethoxylate ltd; CREMOPHOR® CO40, ex BASF and NEODOL® 91-8, ex Shell.

Cationic Polysaccharide. The compositions may further comprise at least one cationic polysaccharide. The cationic polysaccharide can be obtained by chemically modifying polysaccharides, generally natural polysaccharides. By such modification, cationic side groups can be introduced into the polysaccharide backbone The cationic polysaccharides are not limited to: cationic cellulose and derivatives thereof, cationic starch and derivatives thereof, cationic callose and derivatives thereof, cationic xylan and derivatives thereof, cationic mannan and derivatives thereof, cationic galactomannan and derivatives thereof, such as cationic guar and derivatives thereof. Cationic celluloses which are suitable include cellulose ethers comprising quaternary ammonium groups, cationic cellulose copolymers or celluloses grafted with a water-soluble quaternary ammonium monomer.

The cellulose ethers comprising quaternary ammonium groups are described in French patent 1,492,597 and in particular include the polymers sold under the names "JR" (JR 400, JR 125, JR 30M) or "LR" (LR 400, LR 30M) by the company Dow. These polymers are also defined in the CTFA dictionary as hydroxyethylcellulose quaternary ammoniums that have reacted with an epoxide substituted with a trimethylammonium group. Suitable cationic celluloses also include LR3000 KC from Solvay. The cationic cellulose copolymers or the celluloses grafted with a water-soluble quaternary ammonium monomer are described especially in U.S. Pat. No. 4,131,576, such as hydroxyalkylcelluloses, for instance hydroxymethyl-, hydroxyethyl- or hydroxypropylcelluloses grafted especially with a methacryloyl-ethyltrimethylammonium, methacrylamidopropyltrimethylammonium or dimethyl-diallylammonium salt.

The commercial products corresponding to this definition are more particularly the products sold under the names CELQUAT® L 200 and CELQUAT® H 100 by Akzo Nobel. Cationic starches suitable for the present disclosure include the products sold under POLYGELO® (cationic starches from Sigma), the products sold under SOFTGEL®, AMYLOFAX® and SOLVITOSE® (cationic starches from Avebe), CATO from National Starch. Suitable cationic galactomannans can be those derived from Fenugreek Gum, Konjac Gum, Tara Gum, *Cassia* Gum or Guar Gum.

The cationic polysaccharide, of the present disclosure may have an average Molecular Weight (Mw) of between 100,000 daltons and 3,500,000 daltons, preferably between 100,000 daltons and 1,500,000 daltons, more preferably between 100,000 daltons and 1,000,000 daltons.

The fabric conditioner composition of the present disclosure preferably comprises from 0.01 to 2 wt % of cationic polysaccharide based on the total weight of the composition. More preferably, 0.025 to 1 wt % of cationic polysaccharide based on the total weight of the composition. Most preferably, 0.04 to 0.8 wt % of cationic polysaccharide based on the total weight of the composition. In the context of the present application, the term "Degree of Substitution (DS)" of cationic polysaccharides, such as cationic guars, is the average number of hydroxyl groups substituted per sugar unit. DS may notably represent the number of the carboxymethyl groups per sugar unit. DS may be determined by titration.

The DS of the cationic polysaccharide is preferably in the range of 0.01 to 1, more preferably 0.05 to 1, most preferably 0.05 to 0.2. In the context of the present application, "Charge Density (CD)" of cationic polysaccharides, such as cationic guars, means the ratio of the number of positive charges on a monomeric unit of which a polymer is comprised to the molecular weight of said monomeric unit. CD of the cationic polysaccharide, such as the cationic guar, is preferably in the range of 0.1 to 3 (meq/gm), more preferably 0.1 to 2 (meq/gm), most preferably 0.1 to 1 (meq/gm).

Non-ionic Polysaccharide. The fabric conditioner composition may further comprise at least one non-ionic polysaccharide. The nonionic polysaccharide can be a modified nonionic polysaccharide or a non-modified nonionic polysaccharide. The modified non-ionic polysaccharide may comprise hydroxyalkylation and/or esterification. In the context of the present disclosure, the level of modification of non-ionic polysaccharides can be characterized by Molar Substitution (MS), which means the average number of moles of substituents, such as hydroxypropyl groups, per mole of the monosaccharide unit. MS can be determined by the Zeisel-GC method, notably based on the following literature reference: Hodges, et al. (1979) *Anal. Chem.* 51 (13). Preferably, the MS of the modified nonionic polysaccharide is in the range of 0 to 3, more preferably 0.1 to 3 and most preferably 0.1 to 2.

The nonionic polysaccharide of the present disclosure may be especially chosen from glucans, modified or non-modified starches (such as those derived, for example, from cereals, for instance wheat, corn or rice, from vegetables, for instance yellow pea, and tubers, for instance potato or cassava), amylose, amylopectin, glycogen, dextrans, celluloses and derivatives thereof (methylcelluloses, hydroxyalkylcelluloses, ethylhydroxyethylcelluloses), mannans, xylans, lignins, arabans, galactans, galacturonans, chitin, chitosans, glucuronoxylans, arabinoxylans, xyloglucans, glucomannans, pectic acids and pectins, arabinogalactans, carrageenans, agars, gum Arabics, gum tragacanths, ghatti gums, karaya gums, carob gums, galactomannans suchas guars and nonionic derivatives thereof (hydroxypropyl guar), and mixtures thereof.

Among the celluloses that are especially used are hydroxyethylcelluloses and hydroxypropylcelluloses. Suitable non-limiting examples include products sold under the trade names KLUCEL® EF, KLUCEL® H, KLUCEL® LHF, KLUCEL® MF and KLUCEL® G by Aqualon, and CELLOSIZE® Polymer PCG-10 by Amerchol, and HEC, HPMC K200, HPMC K35M by Ashland.

The fabric conditioner composition of the present disclosure preferably comprises from 0.01 to 2 wt % of non-ionic polysaccharide based on the total weight of the composition. More preferably, 0.025 to 1 wt % of non-ionic polysaccharide based on the total weight of the composition. Most preferably, 0.04 to 0.8 wt % of non-ionic polysaccharide based on the total weight of the composition. Preferably the fabric conditioning composition comprises combined weight of the cationic polysaccharide and non-ionic polysaccharide of 0.02 to 4 wt %, more preferably 0.05 to 2 wt % and most preferably 0.08 to 1.6 wt %. Preferably the ratio of the weight of the cationic polysaccharide in the composition and the weight of the nonionic polysaccharide in the composition is between 1:10 and 10:1, more preferably, between 1:3 and 3:1.

In a preferred embodiment, the cationic polysaccharide and non-ionic polysaccharide are mixed prior to addition to the fabric conditioner composition. Preferably the mix is prepared as a suspension in water. Preferably, the ratio of the weight of the quaternary ammonium compound in the composition and the total weight of the cationic polysaccharide and the nonionic polysaccharide in the composition is between 100:1 and 2:1, more preferably, between 30:1 and 5:1. Water. The fabric conditioner composition of the present disclosure comprises water. The compositions are rinse-added softening compositions suitable for use in a laundry process. The compositions are pourable liquids. The liquid compositions have a pH ranging from about 2.0 to about 7, preferably from about 2 to about 4, more preferably from about 2.5 to about 3.5. The compositions may also contain pH modifiers preferably hydrochloric acid, lactic acid or sodium hydroxide. The composition is preferably a ready-to-use liquid comprising an aqueous phase. The aqueous phase may comprise water-soluble species, such as mineral salts or short chain ($C_1$-$C_4$) alcohols. The composition is preferably for use in the rinse cycle of a home textile laundering operation, where, it may be added directly in an undiluted state to a washing machine, e.g., through a dispenser drawer or, for a top-loading washing machine, directly into the drum. The compositions may also be used in a domestic hand-washing laundry operation.

The fabric conditioner composition may comprise other ingredients of fabric conditioner liquids as will be known to the person skilled in the art. Among such materials there may be mentioned: antifoams, perfumes and fragrances (both free oil and encapsulated material), insect repellents, shading or hueing dyes, preservatives (e.g., bactericides), pH buffering agents, perfume carriers, hydrotropes, anti-redeposition agents, soil-release agents, polyelectrolytes, anti-shrinking agents, anti-wrinkle agents, anti-oxidants, dyes, colorants, sunscreens, anti-corrosion agents, drape imparting agents, anti-static agents, sequestrants and ironing aids. The fabric care compositions of the present disclosure may contain pearlisers and/or opacifiers. A preferred sequestrant is HEDP, an abbreviation for etidronic acid or 1-hydroxyethane 1,1-diphosphonic acid.

The fabric conditioner composition may typically be made by combining a melt comprising the fabric softening agent with an aqueous phase. The polymer may be combined with the water phase, or it may be post dosed into the composition after combination of the melt and water phase. A preferred method of preparation is as follows:

1. Heat water to about 40 to 50° C., preferably above 45° C.
2. Add the rheology modifiers to the water slowly, preferably over about 1 minute with stirring.
3. Mix thoroughly, preferably from 1 to 10 minutes.
4. Add any minor ingredients, such as antifoams, sequestrants and preservatives.
5. Melt the softening active and optional fatty alcohol together to form a co-melt.
6. Add the co-melt to the heated water.
7. Add acid to the preferred pH, if required.
8. Add dyes and perfumes.
9. Cool.

Alternatively, but less preferably, the acid may be added at step 4 and/or the minor ingredients may be added after step 6. The addition of the fragrance microcapsules can be added at any stage within the process. It is preferable to add the fragrance microcapsules before the co-melt and more preferable to add the fragrance microcapsules before step 2. However, it is also possible to add the fragrance microcapsules after the co-melt has been added either as the received slurry or the slurry can be diluted with water (1:1 to 10:1 [water:slurry]) before the mixture is cooled. After the mixture has been cooled to below 40° C. as the received slurry or the slurry can be diluted with water (1:1 to 10:1 [water: slurry]) or as a dispersion of the fragrance microcapsule slurry and fragrance oil.

B) Liquid dish detergents such as those described in U.S. Pat. Nos. 6,069,122 and 5,990,065.

C) Automatic Dish Detergents such as those described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562.

D) All-purpose cleaners including bucket dilutable cleaners and toilet cleaners, bathroom cleaners, bath tissue, rug deodorizers, candles (e.g., scented candles), room deodorizers, floor cleaners, disinfectants, window cleaners, garbage bags/trash can liners, air fresheners (e.g., room deodorizer, car deodorizer, sprays, scent oil air freshener, automatic spray air freshener, and neutralizing gel beads), moisture absorber, household devices (e.g., paper towels and disposable wipes), and moth balls/traps/cakes.

E) Personal care products: cosmetic or pharmaceutical preparations. More specifically personal cleansers (e.g., bar soaps, body washes, and shower gels), in-shower conditioner, sunscreen (e.g., sprays, lotions and sticks), insect repellents, hand sanitizers, anti-inflammatory (e.g., balms, ointments and sprays), antibacterial (e.g., ointments and creams), sensates, deodorants and antiperspirants (including aerosol, pump spray and wax based), lotions, body powder and foot powder, body mist or body spray, shave cream and male groom products, bath soak, exfoliating scrub.

F) Hair Care products. More specifically, shampoos (liquid and dry powder), hair conditioners (rinse-out conditioners, leave-in conditioners, and cleansing conditioners), hair rinses, hair refreshers, hair perfumes, hair straightening products, hair styling products, hair fixative and styling aids, hair combing creams, hair wax, hair foam, hair gel, non-aerosol pump spray, hair bleaches, dyes and colorants, perming agents, and hair wipes.

In particular aspects, the core-shell microcapsule composition of this disclosure is of use in improving a freshness impression to a fabric. Accordingly, in certain aspects, the microcapsules of the present disclosure are included in a fabric conditioner or softener having a pH of from 2 to 4, preferably a pH of from 2.5 to 3.5.

The invention is described in greater detail by the below non-limiting examples. Without further elaboration, it is believed that one skilled in the art can, based on the description herein, utilize the present invention to its fullest extent. All publications cited herein are incorporated by reference in their entirety.

Test Methods

The following assays set forth must be used in order that the invention described and claimed herein may be more fully understood.

Test Method 1: Measurement of Emulsion Droplet Size and Capsule Size

Mean emulsion droplet size and capsule diameter were determined at 25° C. with a Malvern Zetasizer ZSP (Worcestershire, U.K.) using a 173° backscattering angle. Capsule size was measured after the addition of HMDA and 4 hours of reaction at 80° C. Dynamic light scattering (DLS) measures the Brownian motion of particles and correlates this movement to an equivalent hydrodynamic diameter (reported as z-average). Prior to DLS measurements, emulsion or capsule slurry was diluted 100-fold with deionized water to avoid multiple scattering effects. Deionized water was filtered through a 0.45 μm polytetrafluoroethylene (PTFE) syringe filter and pre-equilibrated at 25° C. before dilution. All measurements were performed at least with three samples.

Test Method 2: Microencapsulation Efficiency (EE)

The concentration of free oil was determined by performing a 15-minute hexane extraction on the capsules. The surface oil extracted from the hexane wash was analyzed by GC. The percentage of free oil was then extrapolated from a standard calibration curve prepared by using the neat oil.

Test Method 3: Measurement of Residual Monomer Concentrations after the Reaction The residuals concentrations of HMDA and DGEDP-methyl and DGEDP-PEG1 esters were measured using LC-MS. For DGEDP-methyl and DGEDP-PEG1 residuals, capsules were treated with methanol to extract unreacted DGEPD-methyl and DGEDP-PEG1 from the capsule core for the analysis.

Test Method 4: Direct Deposit in Fabric Conditioner or Liquid Laundry Detergent Performance Evaluation For direct deposit performance evaluation, the biobased epoxide microcapsules were added in the base (e.g., fabric conditioner or liquid laundry detergent), at a neat oil equivalence (NOE) of 0.6%. As a control either neat fragrance or melamine formaldehyde capsules were added to the base at 0.6% NOE to match that of the experimental capsules. The samples were mixed well. A 0.125 g aliquot of the base containing fragrance sample was added to 125 g of water. This diluted solution was representative of the concentration typically observed in the rinse liquor of an EU machine wash. Then 5 g of the sample mixture was pipetted on each side of a 4"×5" terry cloth swatch for a total of 10 g of diluted capsule sample. The samples were then air-dried overnight at room temperature and evaluated the next day using headspace analysis to detect the release of total volatiles from the fragrance upon activation of the delivery system by rubbing of the towels to release the fragrance). The headspace of the collected samples was then compared against other samples to assess performance of the biobased epoxide capsules.

Test Method 5: Full Sensory Wash Evaluation

For the full sensory wash evaluation, the biobased epoxide microcapsules were added to 35 g of the base (liquid laundry detergent), at a neat oil equivalence (NOE) of 0.2%. A sample with same NOE was also prepared using neat oil as a control. The samples were mixed well and washed with a European washing machine (Miele). Samples were then removed from the washing machine and line dried overnight. The samples were evaluated using trained judges at three different stages, "pre," which is the sample without any activation, "smooth and fold," where the sample is folded in half, smoothed by swiping the bottom of one's palm firmly from left to right across the towel and smelling for fragrance release. The sample may be folded and smelled a second time for further evaluation. Finally, "post rub" was conducted where the towel was picked up using both hands and vigorously rubbed and smelled for signs of release fragrance.

Test Method 6: Sample Preparation for Biodegradability Evaluation

In order to ensure a clear and accurate understanding of the composition of the capsule shells, the capsules were subjected to a vigorous cleaning process to purify the capsule shells before the biodegradability evaluation. The objective of the cleaning process is to remove materials that are not part of the capsule shells and/or are not tightly associated with the capsule shells.

Cleaning Process of the Present Disclosure

The preferred cleaning process according to the present disclosure is as follows:

1. Washed 300 grams capsule slurry 2 times with water, and then centrifuged at 6000 rpm for 15 minutes (Sorvall LYNX 6000 Superspeed Centrifuge, 1000 g centrifuge bottle, G-force of 7808). Fragrance capsules formed a layer of cake and settled on the topmost layer after centrifugation.
2. The aqueous layer and the precipitation layer were pumped out by a peristatic pump at 300 rpm (MASTERFLEX® L/S Model 77200-62).
3. Repeated water wash 2 more times.
4. The damp capsule cake was collected and freeze dried to remove water.
5. Dry fragrance capsules were subject to methanol extraction at 65° C. (50 grams dry capsule in 300 mL methanol, BÜCHI® Universal Extractor E-800) multiple times until the residual fragrance in the purified walls was less than 2% (w/w) as measured by gas chromatography. Alternatively, in the above procedure, ethyl acetate can be substituted for the methanol. In that case the extraction is carried out at 77° C.
6. The cleaned capsule walls were vacuum dried at 30° C. until fully dried and were then used in the biodegradability evaluation.

EXAMPLES

The following examples are provided to further illustrate the invention and are not to be construed as limitations of the invention, as many variations of the present invention are possible without departing from its spirit or scope.

Example 1: Materials and Synthesis of Biobased Epoxides

Materials. Diphenolic acid (>98%) and epichlorohydrin (>99%) were purchased from TCI America and were used as received. Methanol, hydrochloric acid, sodium bicarbonate, magnesium sulfate, sodium hydroxide, perchloric acid solution (0.1 N in acetic acid), tetraethylammonium bromide, hexamethylenediamine (HMDA), 2,3-dichlorotoluene, 1,6-hexane-1,1,6,6-$d_4$-diamine, and all solvents (e.g., ethyl acetate, isopropanol, dichloromethane) were purchased from Sigma-Aldrich and used as received. Fragrance oil was provided by International Flavors & Fragrances, Inc. Polyvinyl alcohol (PVA, 17.1 KDa) was sold under the tradename Ultalux FP (Sekisui Chemical CO., LTD). 10 wt % polyvinylpyrrolidone (PVP) was sold under the tradename LUVISKOL® K80 (525.2 KDa) (BASF). 10 wt % polyquaternium-11 aqueous solution was sold under the tradename LUVIQUAT® PQ11 (123.1K Da) (BASF). Gum Arabic (GA, 71.2K Da) was from Nexira. The fragrance oil contained 80 wt % Fragrance A oil (hydrophobic fragrance oil) and 20 wt % caprylic/capric triglyceride oil sold under the tradename NEOBEE® M-5. Sophorolipid butyl ester (SLBE) preparation from lactonic sophorolipid (LSL) via ring-opening transesterification with butanol, under alkaline conditions, was prepared according to a known method (Wang, et al. (2020) *ACS Appl. Bio Mater.* 3(8):5136-5147). Spectral characterization by $^1$H and $^{13}$C NMR along with mass spectral analysis of SLBE was consistent with that previously published. (Bisht, et al. (1999) *J. Org. Chem.* 64:780-789).

Synthesis of Methyl Diphenolate Ester and Epoxy Resin. Synthesis of methyl diphenolate ester and the corresponding diepoxy resin (DGEDP-methyl ester) were performed according to a known method (Maiorana, et al. (2015) *Biomacromolecules* 16(3):1021-1031). Briefly, methyl diphenolate ester was prepared with diphenolic acid and methanol through Fischer esterification. The obtained product was a white solid with a melting point of 135° C. Methyl diphenolate ester was then reacted with epichlorohydrin (15 equiv.) under alkaline conditions to prepare DGEDP-methyl ester (Scheme 1).

SCHEME 1

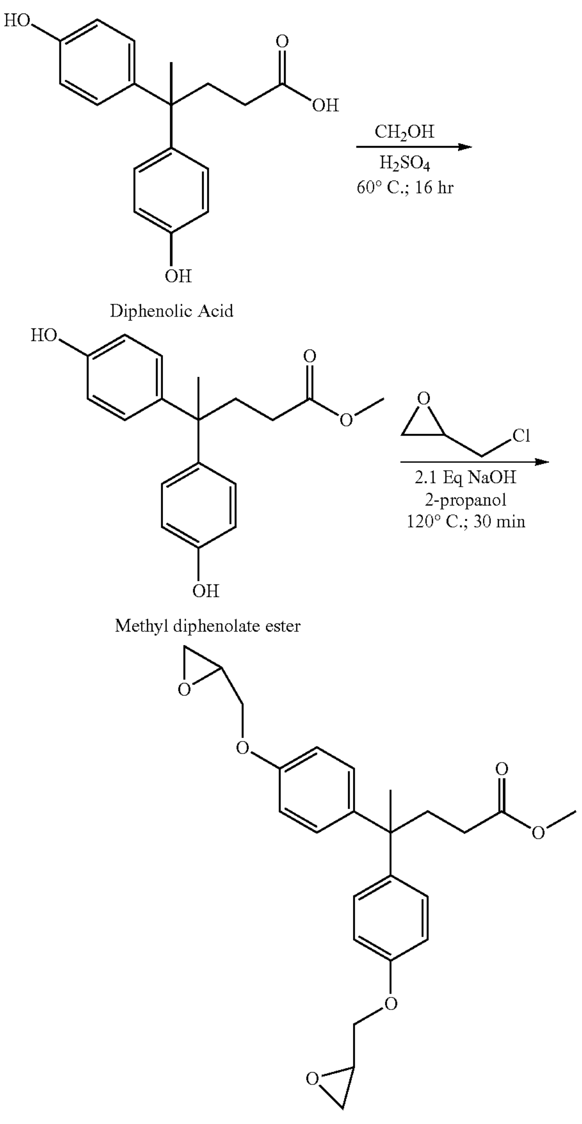

Diphenolic Acid

Methyl diphenolate ester

DGEDP-methyl ester

The product obtained in 90% yield was a viscous light-yellow liquid. Experimental values of epoxide equivalent weights (EEW) for DGEDP-methyl ester were determined according to ASTM D1652. In summary, the sample (0.4 g) was dissolved in dichloromethane to which a solution of tetraethylammonium bromide in acetic acid, and crystal violet (the indicator) was added. Samples were titrated in triplicate using a standardized perchloric acid solution (0.1 N in acetic acid) and the endpoint was determined when the color of the solution turned from blue to green for longer than 30 seconds. The experimental EEW of DGEDP-methyl ester was determined to be 216±8.5 g. Spectral characterization by 1H and 13C NMR along with mass spectral analysis of DGEDP-methyl ester was consistent with that previously published (Maiorana, et al. (2015) *Biomacromolecules* 16 (3):1021-1031).

Example 2: Preparation of Epoxy Resin Microcapsules Using Varied Emulsifiers

To prepare epoxy resin microcapsules, an aqueous solution containing each surfactant was first prepared. PVA or GA was dissolved in deionized water to prepare the surfactant solution at concentrations of 0.5 wt % to 3.5 wt %. Dissolution of PVA was achieved by applying heat (90° C.) for 30 minutes with stirring. PVP and PQ-11 aqueous solutions (both 10 wt %) were diluted with deionized water and combined such that the mass ratio was 1:1 and the total concentration of the two components was varied from 0.5 wt % to 3.5 wt %. Due to its limited water solubility, SLBE was prepared at concentrations of 0.5 wt % to 1.5 wt %. For the internal phase (oil phase), 1 wt % to 4 wt % DGEDP-methyl ester was dispersed in 20 wt % fragrance oil (4:1 w/w Fragrance A: caprylic/capric triglyceride oil) at 60° C. to prepare the core material. A selected surfactant solution and the oil phase were combined and homogenized with IKA T25 shear homogenizer with mixing at 6500 rpm for 2 minutes to form o/w emulsions. The second monomer, hexamethylenediamine (HMDA), was dissolved in deionized water to prepare the HMDA stock solution (40% w/w), which was slowly added to o/w emulsions to achieve a final concentration of 0.75 wt % to 1.25 wt % HMDA. All weight percentages (wt %) are based on the total emulsion weight. Interfacial polymerizations were carried out at 80° C. for 4 hours with gentle stirring (500 rpm). The detailed formulas of each component are shown in Table 1.

TABLE 1

Epoxy Resin Microcapsules

| | GA (wt %) | PVP/PQ-11[b] (wt %) | PVA (wt %) | SLBE (wt %) |
|---|---|---|---|---|
| Surfactant | 0.5 to 3.5 | 0.5 to 3.5 | 0.5 to 3.5 | 0.5, 1, 1.5 |
| Oil[a] | 20 | 20 | 20 | 20 |
| DGEDP-methyl ester | 1, 2, 3, 4 | 2 | 2 | 2 |
| HMDA | 0.75, 1, 1.25 | 1 | 1 | 1 |

All weight percentages are based on total emulsion weight (10 g for each sample). Weight of water = 10 g − $weight_{surfactant}$ − $weight_{oil}$ − $weight_{DGEDP\ methyl\ ester}$ − $weight_{HMDA}$.

[a]Oil used in this work consisted of both Fragrance A (fragrance oil) and caprylic/capric triglyceride oil at a mass ratio of 4:1.

[b]PVP/PQ-11 cosurfactant system contained both PVP and PQ-11 with a mass ratio of 1:1. The wt % values listed in Table 1 under PVP/PQ-11 are the total of each component.

Example 3: Preparation of Epoxy Resin Microcapsules Using Polyamines

Capsules can also be prepared by using these single polyamines including hexamethylenediamine (HMDA), triethylenetetramine (TETA), branched polyethyleneimine (BPEI), urea, guanidine carbonate, or chitosan oligosaccharide (COS). To prepare microcapsules with single polyamines, a 25% stock solution of the gum Arabic was prepared by dissolving the gum Arabic into deionized water. The gum Arabic was further diluted into the aqueous phase so that the overall concentration of the gum Arabic was 2.5 wt % of the overall formulation. A fragrance core prepared from fragrance alone or fragrance in combination with a co-solvent (co-solvents included NEOBEE® oil or white mineral oil). The DGEDP-R was then heated in an oven at 60° C. for 10-20 minutes to allow the DGEDP-R to become flowable. The hot DGEDP-R was then added to the oil phase, mixed until the sample appeared homogeneous (approximately 5 minutes with stirring) and used immediately to prepare the emulsion. DGEDP-R was added so that the final concentration in the formula was 1-4%.

The emulsion solution and the oil phase were combined and homogenized with IKA T25 shear homogenizer with mixing at 6500 rpm for 3 minutes to form o/w emulsions. Monomers included hexamethylenediamine (HMDA), triethylenetetramine (TETA), branched polyethyleneimine (BPEI), urea, guanidine carbonate, or chitosan oligosaccharide (COS). To add the polyamine monomers, the monomers were diluted at the following concentrations using deionized water (wt/wt %): HMDA at 40%, TETA at 60%, urea at 25%, guanidine carbonate at 20%, COS at 25%, and BPEI at 30%. Individual polyamine solutions were slowly added to o/w emulsions to achieve a final concentration of 0.5-2 wt % HMDA in the overall formulation. All weight percentages were based on the total emulsion weight. Interfacial polymerizations were carried out at 80° C. for 4 hours at pH 11 unless otherwise noted with gentle stirring (350-500 rpm). In some cases, an additional 18 hr cure at 80° C. was added to bring the reaction to further completeness.

Example 4: Preparation of Epoxy Resin Microcapsules Using Combinations of Polyamines and/or Biopolymers To prepare microcapsules with combinations of polyamines, the following procedure was followed. A 25% stock solution of the gum Arabic was prepared by dissolving the gum Arabic into deionized water. The gum Arabic was further diluted into the aqueous phase so that the overall concentration of the gum Arabic was 2.5 wt % of the final emulsion formulation. Next, a fragrance core was prepared using a mixture of fragrance and a co-solvent (NEOBEE® oil). Total wt % of the fragrance and NEOBEE® oil in the final emulsion concentration was 16 wt % and 4 wt %, respectively. The DGEDP-R was then heated in an oven at 60° C. for 10-20 minutes to allow the DGEDP-R to become flowable. The hot DGEDP-R was then added to the oil phase, mixed until the sample appeared homogeneous (approximately 5 minutes with stirring) and used immediately to prepare the emulsion. DGEDP-R was added so that the final concentration in the formula was 2%.

The emulsion solution and the oil phase were combined and homogenized with IKA T25 shear homogenizer with mixing at 6500 rpm for 3 minutes to form an o/w emulsion. After creating the emulsion, one of two catalysts were added to the mixture. Either imidazole was added to the emulsion as a 20% stock solution until a final emulsion concentration of 2% was achieved or DABCO was added as a 20% stock solution until a final emulsion concentration of 0.05% was achieved. The emulsion was further reacted by adding two different polyamines. The first polyamine to be added was either the COS or guanidine carbonate. If adding the COS, a solution of 25% COS was prepared and then added slowly to the emulsion while mixing until a concentration of either 1% or 4% COS in the final formulation was achieved. If adding the guanidine carbonate, a solution of 20% guanidine carbonate was prepared and then added slowly to the emulsion while mixing until a concentration of either 1% or 1.75% guanidine carbonate in the final formulation was achieved.

Next, a second polyamine was added in one of two ways. In one case, the second polyamine was added immediately after the first polyamine and then the emulsion was cured at 80° C. for 4 hours with gentle stirring (350-500 rpm). Alternatively, the second polyamine was added after the first polyamine was reacted in the emulsion with DGEDP-R for 2 hours at 80° C. After the 2 hours initial cure, the second polyamine was added to the emulsion and the entire system was cured for an additional 2 hours at 80° C., with mixing. The pH of the emulsion during curing was adjusted to 11 before cure unless otherwise noted. All weight percentages are based on the total emulsion weight.

To prepare microcapsules with the combination of amines and dihydrazides, the following procedure was followed. A 25% stock solution of the gum Arabic was prepared by dissolving the gum Arabic into deionized water. The gum Arabic was further diluted into the aqueous phase so that the overall concentration of the gum Arabic was 2.5 wt % of the final emulsion formulation. Next, a fragrance core was prepared using a mixture of fragrance and a co-solvent (NEOBEE® oil). Total % wt of the fragrance and NEOBEE® oil in the final emulsion concentration was 16% and 4%, respectively. The DGEDP-R was then heated in an oven at 60° C. for 10-20 minutes to allow the DGEDP-R to become flowable. The hot DGEDP-R was then added to the oil phase, mixed until the sample appeared homogeneous (approximately 5 minutes with stirring) and used immediately to prepare the emulsion. DGEDP-R was added so that the final concentration in the formula was 2-4%. The emulsion solution and the oil phase were combined and homogenized with IKA T25 shear homogenizer with mixing at 6500 rpm for 3 minutes to form an o/w emulsion. Polyamines in the provided examples included triethylenetetramine (TETA) and the dihydrazide of focus was adipic dihydrazide. To add the polyamine and dihydrazide monomers, the monomers were diluted at the following concentrations using deionized water (wt/wt %): TETA at 60% and adipic dihydrazide at 10%. Individual polyamine solutions were slowly added to o/w emulsions to achieve a final concentration of 0.5-3.5 wt % in the overall formulation. All weight percentages were based on the total emulsion weight. Interfacial polymerizations were carried out at 80° C. for 4 hours at pH 11 unless otherwise noted with gentle stirring (350-500 rpm). In some cases, an additional 18 hours cure at 80° C. was added to bring the reaction to further completeness.

Example 5: Preparing Capsules with Catalyst Addition

To prepare capsules containing DGEDP-R and COS with additional catalysts, the following procedure was followed. A 25% stock solution of the gum Arabic was prepared by dissolving the gum Arabic into deionized water. The gum Arabic was further diluted into the aqueous phase so that the overall concentration of the gum Arabic would be 2.5% wt of the overall formulation. A fragrance core was prepared using a mixture of fragrance with a co-solvent (NEOBEE® oil) at a ratio of 80/20, respectively, where the total wt % of the final emulsion was 16 wt % fragrance and 4 wt % NEOBEE® oil. The DGEDP-R was then heated in an oven at 60° C. for 10-20 minutes to allow the DGEDP-R to become flowable. The hot DGEDP-R was then added to the oil phase, mixed until the sample appeared homogeneous (approximately 5 minutes with stirring). DGEDP-R was added so that the final concentration in the emulsion formula was 2%. The oil phase with DGEDP-R crosslinker was used immediately to prepare the emulsion. The aqueous solution and the oil phase were combined and homogenized with IKA T25 shear homogenizer with mixing at 6500 rpm for 3 minutes to form o/w emulsions.

The second monomer was added by first diluting COS to a 25% stock solution in deionized water and then the stock solution was added slowly to the o/w emulsions to achieve a final concentration of 1-6 wt % COS in the overall formulation. Next, a catalyst was added to the emulsion while mixing. The catalyst was either imidazole, added as a 40% stock solution, or DABCO, added as a 20% stock solution in deionized water. The catalysts were dosed into the emulsion to achieve final weights of 0.2-4% imidazole or 0.5% DABCO in the emulsion formulation. All weight percentages are based on the total emulsion weight. Interfacial polymerizations were carried out at 80° C. for 4 hours at pH 11 unless otherwise noted with gentle stirring (350-500 rpm).

Example 6: Effect of DGEDP-Methyl Ester/HMDA Ratio on Encapsulation Efficiency and Capsule Morphology The inventors have discovered that encapsulation efficiency can be improved when using high level of DGEDP-R (1-4%) and HMDA (0.5-1.75%). To take this a step further, capsules containing 2% DGEDP-methyl were prepared increasing HMDA concentrations past 1.25%. Table 2 provides data showing both encapsulation efficiency and morphology were affected by the concentration of HMDA used in the formulation. Capsules prepared with DGEDP-methyl crosslinker containing were able to be formed with highest encapsulation efficiency and little to no aggregation if the HMDA levels were at 1.75%. Above 1.75% capsules started to form aggregates which will affect appearance of the encapsulation system when applied in base. Capsules prepared with HMDA levels below 1.75%, showed decrease in encapsulation efficiency which also negatively affected performance (sensory data to follow). Capsules formed with DGEDP-PEG1 (where PEG1=methoxyethanol) using similar conditions to those described above formed with DGEDP-methyl (2% DGEDP-PEG1 and 1.75% HMDA in the formulation) were also successfully encapsulated resulting in high encapsulation efficiencies to DGEDP-methyl. Based on the results, the preferred crosslinkers include DGEDP-methyl and DGEDP-PEG1.

TABLE 2

Summary of the effect of Epoxide and amine crosslinker on encapsulation efficiency and capsule morphology*

| | Capsule formulation | | | | | | Capsule Characterization | |
|---|---|---|---|---|---|---|---|---|
| | Emulsifier | | DGEDP-R | | | | % Encapsulation | Capsule |
| Sample | Type | % | R group | % | % HMDA | | Efficiency | Appearance |
| 66C | Gum Arabic | 2.5 | Methyl | 2 | 1 | | >25 | Individual capsules |
| 70A | Gum Arabic | 2.5 | Methyl | 2 | 1.25 | | 92 | Individual capsules |
| 70B | Gum Arabic | 2.5 | Methyl | 2 | 1.50 | | 96.5 | Individual capsules |
| 70C | Gum Arabic | 2.5 | Methyl | 2 | 1.75 | | 99 | Individual capsules |
| 50C | Gum Arabic | 2.5 | Methyl | 2 | 2 | | 89.5 | Aggregated |
| 71K | Gum Arabic | 2.5 | PEG1 | 2 | 1.75 | | 98.5 | Individual capsules |

*The % wt of the materials in the total capsule formulation are listed in the table. Note capsules contained: 20% Fragrance A and 4% NEOBEE ® oil.

The conversion of the reaction can be improved by using the lower DGEDP-R levels and higher HMDA levels leading to low residual levels of DGEDP-R which can be safely used in consumer products (e.g., liquid laundry detergent). For example, capsules prepared with 1.75% HDMA and 2% DGEDP-methyl or PEG1 resulted in <1 ppm of the bioepoxide crosslinker residuals in the final product base.

Example 7: Selection of Co-Solvent or Core Modifier for Active Material

Similar capsules to those prepared with formula from 70° C. were then evaluated by preparing capsules with varied co-solvent types and fragrance to co-solvent ratios. Co-solvent effect was evaluated by combining select co-solvents with a standard fragrance ingredient to evaluate changes in free oil and appearance of capsule formed when using either DGEDP-methyl or PEG1 crosslinkers with HMDA and gum Arabic as an emulsifier.

The results (Table 3) indicated that hydrophobic co-solvents were more beneficial to providing capsules resulting in low free oil (white mineral oil or caprylic/capric triglyceride oil (sold under the tradename NEOBEE®, c Log p<10)) while more hydrophilic co-solvents (triethyl citrate, c Log p=1.2) resulted in weak capsules with higher free oil. Having capsules with higher fragrance to co-solvent ratios also aided in mitigating capsule aggregation which was especially apparent with capsules prepared with DGEDP-PEG1.

TABLE 3

Core Modifier effect on Encapsulation

| Sample | Co-solvent[a] | Fragrance[a] | Cross-linker | Free oil | Capsule Appearance |
|---|---|---|---|---|---|
| 71D | 12% NEOBEE oil | 12% | PEG1 | 0.7% | Aggregated |
| 71I | 12% WMO | 12% | PEG1 | 1% | Individual capsules |
| 71J | 4.8% WMO | 19.2% | PEG1 | 0.2% | Individual capsules |

TABLE 3-continued

| Core Modifier effect on Encapsulation | | | | | |
|---|---|---|---|---|---|
| Sample | Co-solvent[a] | Fragrance[a] | Cross-linker | Free oil | Capsule Appearance |
| 71K | 4.8% NEOBEE ® oil | 19.2% | PEG1 | 0.3% | Individual capsules |
| 71L | 0% | 24% | PEG1 | 0.5% | Individual capsules |
| 71H | 12% Triethyl citrate | 12% | PEG1 | >5% | Weak capsules |
| 710 | 12% NEOBEE ® oil | 12% | Methyl | 0.2% | Individual capsules |
| 71N | 12% WMO | 12% | Methyl | 0.7% | Individual capsules |
| 71P | 4.8% WMO | 19.2% | Methyl | 0.1% | Individual capsules |
| 71Q | 4.8% NEOBEE ® oil | 19.2% | Methyl | 0.2% | Individual capsules |

Capsules were prepared with 2% of the DGEDP-R crosslinker, 1.75% HMDA and 2.5% gum Arabic. The oil phase was added to the aqueous phase and homogenized at 6500 RPM and pH adjusted to 11 with NaOH, then cured at 80° C. for 4 hours while mixing.
WMO = white mineral oil.
[a]% wt. of the materials in the total capsule formulation.

Example 8: Effect of Catalyst on COS Reaction with DGEDP-R

The inventors have found that the addition of a catalyst can improve capsule formation and reduction of free oil when crosslinking Chitosan Oligosaccharide (COS) with DGEDP-PEG. The results of using imidazole as a catalyst is listed in Table 4 and indicates that the DGEDP-R reaction with COS appeared to be catalyzed by imidazole when added at 2%. Lower amounts (0.02%) of imidazole result in breakage. Notably, replacing gum Arabic with PVP/PQ-11 provided an improvement in reducing free oil. However, capsules prepared with PVP/PQ-11 were not very homogeneous and aggregated.

TABLE 4

| Effect of Catalyst on Capsules Containing COS | | | | | | |
|---|---|---|---|---|---|---|
| Sample | R group | COS[a] | Emul.[a] | Cat.[a] | pH | Free oil |
| 74A | Me | 1% | 2.5% GA | 0.2% Im | 8 | >10% |
| 74D | Me | 1% | 2.5% GA | 2% Im | 8 | 4.2% |
| 74N | Me | 1% | 0.25% PPV/ 0.25% PQ-11 | 2% Im | 11 | 2.5% |

Capsules contained 16% Fragrance and 4% NEOBEE ® oil in addition to the above-referenced components.
The oil phase was added to the aqueous phase and homogenized at 6500 RPM and pH was adjusted to 11 with NaOH.
Capsules were cured 80° C. for 4 hours while mixing.
Me = methyl; Emul. = emulsifier; GA = gum Arabic; Cat = catalyst; and Im = Imidazole.
[a]% wt. of the materials in the total capsule formulation.

Example 9: Effect of Combinations of Polyamines on Capsule Formation

The inventors have also found that a combination of HMDA with either Chitosan Oligosaccharide (COS) or Guanidine carbonate provide lower free oils and the results are summarized in Table 5. We have also found that this has led to performance in fabric conditioner with increased fragrance release.

TABLE 5

| Combination of Polyamines for Capsules Formation | | | | | | |
|---|---|---|---|---|---|---|
| Sample | R group | 1° polyamine[a] | HMDA[a] | Point of HMDA addition | Cat.[a] | Free oil |
| 74M | Me | 1% COS | — | | 2% Im | 7.2% |
| 74X | Me | 1% COS | 1.75% | With COS | 2% Im | 0.3% |
| 75I | PEG1 | 1% GC | 1% | With guanidine | 0.05% DABCO | 0.4% |
| 75J | PEG1 | 1% GC | 1.75% | With guanidine | 0.05% DABCO | 0.7% |

Capsules contained 16% Fragrance and 4% NEOBEE ® oil in addition to the above-referenced components.
The oil phase was added to the aqueous phase and homogenized at 6500 RPM and pH was adjusted to 8 or 11 with NaOH.
Capsules were cured as indicated.
Me = methyl; GC = Guanidine Carbonate; Cat = catalyst; and Im = Imidazole.
[a]% wt. of the materials in the total capsule formulation.

Example 10: Performance Evaluations of DGEDP-R/HMDA Microcapsules

The DGEDP-R/HMDA capsules (prepared using HMDA as the sole polyamine) were evaluated in liquid laundry detergent using a full sensory evaluation as described in the methods section. A description of the capsules is provided in Table 6.

TABLE 6

| Capsules Formulae Description | | | | | |
|---|---|---|---|---|---|
| Capsule | DGEDP-R | Amine | Emulsifier | Frag. | Co-solvent |
| 71J | 2% DGEDP-PEG1 | 1.75% HMDA | 2.5% GA | 19.2% | 4.8% WMO |
| 71K | 2% DGEDP-PEG1 | 1.75% HMDA | 2.5% GA | 19.2% | 4.8% NEOBEE ® |
| 71P | 2% DGEDP-Me | 1.75% HMDA | 2.5% GA | 19.2% | 4.8% WMO |
| 71Q | 2% DGEDP-Me | 1.75% HMDA | 2.5% GA | 19.2% | 4.8% NEOBEE ® |

All % are based on % wt. of the materials in the total capsule formulation.
Me = methyl; GA = gum Arabic; and WMO = white mineral oil.

Full sensory performance data were obtained for capsules as provided in Table 6 dosed into liquid laundry detergent and applied via a full wash method onto cloths and subsequently evaluated for pre-, smooth and fold, and post-rub performance. Results of the sensory evaluation are provided in Table 7.

TABLE 7

| Full Wash Sensory Performance of Capsules in Liquid Laundry Detergent | | | |
|---|---|---|---|
| Sample | Pre (Std. Error) | Smooth & fold (Std. Error) | Post Rub (Std. Error) |
| Neat (0.2% NOE) | 2.94 (1.14) | 3.04 (1.17) | 3.26 (1.18) |
| Comparative MF capsule (0.04% NOE) | 2.64 (1.16) | 3.15 (1.16) | 4.29 (1.14) |
| Sample 71P | 3.81 (1.15) | 5.67 (1.12) | 7.95 (1.12) |
| Sample 71Q | 3.62 (1.13) | 5.02 (1.14) | 7.39 (1.11) |
| Sample 71J | 2.46 (1.17) | 3.01 (1.16) | 4.50 (1.16) |
| Sample 71K | 2.97 (1.16) | 3.47 (1.17) | 4.68 (1.17) |

Capsules containing 2% DGEDP-R and 1.75% HMDA performed well in a full wash liquid laundry detergent sensory evaluation. Specifically, samples 71J and 71K containing DGEDP-PEG1 as the crosslinker both showed a benefit over neat and similar performance to commercial capsules when dosed in liquid laundry detergent and evaluated in a full sensory evaluation on hand towels (see Table 7). Samples 71Q and 71P containing DGEDP-Methyl as the crosslinker showed a benefit over neat and outperformed commercial capsules when dosed in liquid laundry detergent in a full sensory evaluation on hand towels (see Table 7). Co-solvents used at these levels appeared not to have much effect in the performance of these particular capsule variations.

Example 11: Performance Evaluations of DGEDP-R/HMDA with COS/Guanidine Carbonate Microcapsules Capsules prepared using DGEDP-R with HMDA in combination with either COS or Guanidine carbonate were evaluated using headspace measurements by directly depositing the capsules on a surface as determined in accordance with the protocol described in the Methods Section. A description of the capsules is provided in Table 8. Results of the sensory evaluation are provided in Table 9.

TABLE 8

Capsules Formulae Description

| Sample | DGEDP-R | Amine | Catalyst/pH | Frag. | Co-solvent |
|---|---|---|---|---|---|
| 74X | 2% DGEDP-Me | 1% COS/ 1.75% HMDA | 2% Imidazole/11 | 16% | 4% NEOBEE ® |
| 75I | 2% DGEDP-PEG | 1% GC/ 1% HMDA | 0.05% DABCO/11 | 16% | 4% NEOBEE ® |
| 75J | 2% DGEDP-PEG | 1% GC/ 1.75% HMDA | 0.05% DABCO/11 | 16% | 4% NEOBEE ® |

All % are based on % wt. of the materials in the total capsule formulation.
Me = methyl; COS = Chitosan Oligosaccharide; and GC = guanidine carbonate.
For all samples HMDA was added simultaneously with the COS or guanidine carbonate.

TABLE 9

Performance Data of Capsules in Fabric Conditioner

| Sample [1] | Avg Post Rub Headspace (ppb) |
|---|---|
| Neat | 107 |
| 74X | 3,260 |
| 75I | 1365 |
| 75J | 635 |

[1] Each sample was dosed at 0.6% neat oil equivalence in base. Headspace performance data were obtained for capsules dosed into a fabric conditioner and applied via direct deposit method onto cloths and evaluated for post rub performance.

Samples 74X, 75I and 75J showed a benefit over neat when dosed in fabric conditioner and directly applied to cloth then evaluated for a post rub burst via headspace. The results indicate that by combining HMDA with either COS or guanidine carbonate, there is an increase capsule stability providing added fragrance release in the fabric conditioner base (see Table 9). Like the capsules tested in Table 6, these samples also had provided performance when evaluated in liquid laundry detergent matching the benchmark melamine formaldehyde capsule (data not shown).

Example 12: Biodegradability Evaluation

Capsules prepared using 2.5% Gum Arabic as the emulsifier and 2% DGEDP-PEG1 and 1.75% HMDA as crosslinkers were placed through a water wash, followed by freeze dry and solvent extraction to remove fragrance and obtained cleaned capsule wall according to the process described in Test Method 6. The biodegradation of the capsules was evaluated per protocols described by OECD301F. The capsules were found to reach >60% biodegradation after 45 days (see FIG. 1). This data demonstrates the biodegradable nature of the capsule systems prepared by the present disclosure.

Example 13: Exemplary Production Compositions

Composition I is an example of fine fragrance composition according to the present disclosure. It is prepared by admixture of the components described in Table 10, in the proportions indicated.

TABLE 10

Fine Fragrance Composition

| Ingredient | Composition I (wt %[1]) |
|---|---|
| Ethanol SD-40 | 60-80 |
| Microcapsules[2] | 2.5-25 |
| DI-Water | Qs |
| Total | 100 |

[1] wt % relative to the total weight of the composition.
[2] Encapsulated amount depends on the fragrance loading to 0.3% NOE.

Composition II is an example of fabric conditioner composition according to the present disclosure. It is prepared by admixture of the components described in Table 11, in the proportions indicated.

TABLE 11

Fabric Conditioner Composition

| Ingredient | Composition II (wt %[1, 2]) |
|---|---|
| Platform 12 fabric conditioner base | 90 |
| Microcapsules (Fragrance A)[2] | 0.5-3.0 |
| DI-Water | Qs |
| Total | 100 |

[1] wt % relative to the total weight of the composition.
[2] Encapsulated amount depends on the fragrance loading to 0.2% NOE.

Composition III is an example of liquid detergent composition according to the present disclosure. It is prepared by admixture of the components described in Table 12, in the proportions indicated.

TABLE 12

Liquid Detergent Composition

| Ingredient | Composition III (wt %[1]) |
|---|---|
| Black bull Liquid laundry detergent | 90 |
| Microcapsules (Fragrance A)[2] | 0.5-3.0 |
| DI-Water | Qs |
| Total | 100 |

[1] wt % relative to the total weight of the composition.
[2] Encapsulated amount depends on the fragrance loading to 0.2% NOE.

Composition IV is an example of powder detergent composition according to the present disclosure. It is prepared by admixture of the components described in Table 13, in the proportions indicated.

TABLE 13

| Powder Detergent Composition | |
|---|---|
| Ingredient | Composition IV (wt %[1]) |
| Linear alkylbenzenesulfonate | 22 |
| $C_{12-14}$ dimethylhydroxyethyl ammonium chloride | 0.2 |
| AE3S | 1 |
| Zeolite A | 1 |
| 1.6R silicate ($SiO_2$:$Na_2O$ at ratio 1.6:1) | 5 |
| Sodium carbonate | 20 |
| Polyacrylate MW 4500 | 0.6 |
| Carboxymethyl cellulose | 0.3 |
| STAINZYME ® (20mg active/g) | 0.2 |
| Protease (SAVINASE ®, 32.89 mg active/g) | 0.1 |
| Lipase-LIPEX ® (18 mg active/g) | 0.07 |
| Fluorescent brightener | 0.06 |
| DTPA | 0.8 |
| $MgSO_4$ | 1 |
| Sodium percarbonate | 5.2 |
| TAED | 1.2 |
| Neat Fragrance | 0.5 |
| Microcapsules | 0.5-3.0 |
| Total | 100 |

[1]wt % relative to the total weight of the composition.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A core-shell microcapsule composition comprising:

(i) a microcapsule core comprising an active material; and (ii) a microcapsule shell encapsulating the microcapsule core;

wherein the microcapsule shell comprises a polymer formed with a biobased epoxide and a polyamine, and wherein the biobased epoxide is a diglycidyl ether diphenolic ester.

2. The core-shell microcapsule composition of claim 1, wherein the polyamine is selected from the group consisting of hexamethylene diamine (HMDA), ethylene diamine (EDA), diethylene triamine (DETA), dihydrazide, dipropylenetriamine (norspermidine), triethylene tetramine (TETA), tetraethylene pentamine (TEPA), chitosan oligosaccharide (COS), guanidine carbonate, ε-poly(L-lysine), α-poly(L-lysine), L-lysine containing peptides, L-lysine containing proteins, gelatin, and combinations thereof.

3. The core-shell microcapsule composition of claim 2, wherein the polyamine is selected from the group consisting of hexamethylene diamine (HMDA), chitosan oligosaccharide (COS), guanidine carbonate, and combinations thereof.

4. The core-shell microcapsule composition of claim 3, wherein the polyamine is a combination of HMDA and COS or a combination of HMDA and guanidine carbonate, wherein the weight ratio of HMDA to COS is from 10:1 to 1.5:1, and the weight ratio of HMDA to guanidine carbonate is from 10:1 to 1.5:1.

5. The core-shell microcapsule composition of claim 1, wherein the microcapsule has a mean diameter particle size of from 5 μm to 100 μm as determined by dynamic light scattering.

6. The core-shell microcapsule composition of claim 1, wherein total amount of the active material ranges from 5% to 50% by weight of the core-shell microcapsule composition, and the active material is selected from the group consisting of fragrance, flavor, cosmetic active, malodor counteractant, and combinations thereof.

7. The core-shell microcapsule composition of claim 1, wherein the weight ratio of the active material to the biobased epoxide is from 50:1 to 1:1.

8. The core-shell microcapsule composition of claim 1, wherein the microcapsule shell has a degree of biodegradability of at least 20%, 30%, 40%, 50%, 60%, 65%, 70%, 75%, 80%, 85%, 90%, 95% or 98%, within 60 days according to OECD301F test.

9. The core-shell microcapsule composition of claim 1, wherein the microcapsule shell is inherently primary biodegradable as evidenced by a degree of biodegradability of at least 20% according to OECD 301F test, or ultimately biodegradable as evidenced by a degree of biodegradability of at least 60% according to OECD 301F test.

10. A consumer product comprising the core-shell microcapsule composition of claim 1, wherein the consumer product is a laundry detergent, a liquid laundry detergent, a powder laundry detergent, a tablet laundry detergent, a mono-chamber or multi-chamber unidose detergent, a laundry detergent bar, a laundry detergent cream, a hand wash laundry detergent, a fabric conditioner or softener, a dryer sheet, a fabric refresher, a liquid or solid scent booster, a shampoo, a hair conditioner, a bar soap, a shower gel, a body wash, an antiperspirant, a deodorant, a body spray, a body mist, a lotion, a candle or a textile.

11. A method of preparing a core-shell microcapsule composition of claim 1, comprising:

(a) emulsifying an active material with a biobased epoxide to form an emulsion, wherein the biobased epoxide is a diglycidyl ether diphenolic ester;

(b) adding a polyamine to the emulsion; and (c) providing a condition sufficient to induce interfacial polymerization in the emulsion to form a slurry that comprises core-shell microcapsules each having a microcapsule shell encapsulating a microcapsule core, thereby obtaining the core-shell microcapsule composition of claim 1.

12. The method of claim 11, wherein the emulsion further comprises an emulsifier.

13. The method of claim 11, wherein the condition sufficient to induce interfacial polymerization comprises curing for up to 24 hours.

14. A method for increasing the degree of biodegradability of a core-shell microcapsule, comprising incorporating a polymer into the shell of the core-shell microcapsule to increase the degree of biodegradability of the core-shell microcapsule, wherein the polymer is formed with a biobased epoxide and a polyamine, wherein the biobased epoxide is a diglycidyl ether diphenolic ester, wherein the polymer is formed by interfacial polymerization in an emulsion.

15. The core-shell microcapsule composition of claim 1, wherein the biobased epoxide is selected from the group consisting of diglycidyl ether diphenolic methyl ester, diglycidyl ether diphenolic ethyl ester, diglycidyl ether diphenolic propyl ester, diglycidyl ether diphenolic butyl ester, diglycidyl ether diphenolic pentyl ester, diglycidyl ether diphenolic methoxy PEG, and combinations thereof, wherein the PEG is a PEG having 1 to 10 ethylene oxide units.

16. The method of claim 11, wherein the biobased epoxide is selected from the group consisting of diglycidyl ether diphenolic methyl ester, diglycidyl ether diphenolic ethyl ester, diglycidyl ether diphenolic propyl ester, diglycidyl ether diphenolic butyl ester, diglycidyl ether diphenolic pentyl ester, diglycidyl ether diphenolic methoxy PEG, and combinations thereof, wherein the PEG is a PEG having 1 to 10 ethylene oxide units.

17. The method of claim 11, wherein the polyamine is selected from the group consisting of hexamethylene diamine (HMDA), ethylene diamine (EDA), diethylene triamine (DETA), dihydrazide, dipropylenetriamine (norspermidine), triethylene tetramine (TETA), tetraethylene pentamine (TEPA), chitosan oligosaccharide (COS), guanidine carbonate, ε-poly(L-lysine), α-poly(L-lysine), L-lysine containing peptides, L-lysine containing proteins, gelatin, and combinations thereof.

* * * * *